United States Patent
Liang et al.

(10) Patent No.: US 12,030,037 B2
(45) Date of Patent: Jul. 9, 2024

(54) CATALYST COMPOSITION FOR THE PRODUCTION $C_2$ HYDROCARBONS FROM METHANE

(71) Applicant: SABIC Global Technologies B.V., Bergen op Zoom (NL)

(72) Inventors: Wugeng Liang, Sugar Land, TX (US); David West, Sugar Land, TX (US); Hector Perez, Sugar Land, TX (US); Sagar Sarsani, Sugar Land, TX (US); Luanyi Elizabeth Li, Sugar Land, TX (US)

(73) Assignee: Sabic Global Technologies B.V., Bergen op Zoom (NL)

( * ) Notice: Subject to any disclaimer, the term of this patent is extended or adjusted under 35 U.S.C. 154(b) by 606 days.

(21) Appl. No.: 17/295,931

(22) PCT Filed: Dec. 4, 2019

(86) PCT No.: PCT/IB2019/060439
§ 371 (c)(1),
(2) Date: May 21, 2021

(87) PCT Pub. No.: WO2020/115678
PCT Pub. Date: Jun. 11, 2020

(65) Prior Publication Data
US 2022/0008897 A1 Jan. 13, 2022

Related U.S. Application Data

(60) Provisional application No. 62/774,885, filed on Dec. 4, 2018.

(51) Int. Cl.
*B01J 21/08* (2006.01)
*B01J 23/02* (2006.01)
(Continued)

(52) U.S. Cl.
CPC .............. *B01J 23/30* (2013.01); *B01J 21/08* (2013.01); *C07C 2/84* (2013.01); *C07C 2521/08* (2013.01); *C07C 2523/30* (2013.01)

(58) Field of Classification Search
CPC ... B01J 21/08; B01J 23/02; B01J 23/10; B01J 23/30; B01J 23/78; B01J 23/83; B01J 23/888; C07C 2/84
See application file for complete search history.

(56) References Cited

U.S. PATENT DOCUMENTS 4,130,507 A * 12/1978 Hayes ................... C07C 5/3337
502/220
5,618,505 A * 4/1997 Subramanian ....... B01D 53/945
423/247
(Continued)

FOREIGN PATENT DOCUMENTS

EP 3194070 7/2017
JP 5493928 5/2014
(Continued)

OTHER PUBLICATIONS

Chou, et al., "Catalytic Oxidation of Methane to C2—C4 Hydrocarbons Over $CeO_2$ Promoted $W-Mn/SiO_2$ Catalysts at Higher Pressure," *Journal of Chinese Chemical Society: General*, 51(1): 85-90, 2004.
(Continued)

*Primary Examiner* — Cam N. Nguyen
(74) *Attorney, Agent, or Firm* — Norton Rose Fulbright US LLP

(57) ABSTRACT

A catalyst composition, suitable for producing ethylene and other $C_{2+}$ hydrocarbons, from methane. The composition comprises a blended product of two distinct catalyst components, blended at such synergistic proportions that results in a catalyst having high ethylene selectivity while maintaining low ethyne selectivity and sufficient catalytic activity (Continued)

rate. The invention further provides a method for preparing such a catalyst composition and a process for producing ethylene and other $C_{2+}$ hydrocarbons, using such a catalyst composition.

17 Claims, 2 Drawing Sheets

(51) Int. Cl.
    *B01J 23/10*    (2006.01)
    *B01J 23/30*    (2006.01)
    *B01J 23/78*    (2006.01)
    *B01J 23/83*    (2006.01)
    *B01J 23/888*   (2006.01)
    *C07C 2/84*     (2006.01)

(56) References Cited

U.S. PATENT DOCUMENTS

| | | | | |
|---|---|---|---|---|
| 6,403,523 | B1* | 6/2002 | Cantrell | C01F 17/247 |
| | | | | 502/313 |
| 6,576,803 | B2* | 6/2003 | Cantrell | B01J 23/10 |
| | | | | 558/383 |
| 7,229,945 | B2* | 6/2007 | Kauffman | C07C 45/35 |
| | | | | 502/313 |
| 8,722,940 | B2* | 5/2014 | Kauffman | B01J 37/009 |
| | | | | 568/477 |
| 11,813,592 | B2* | 11/2023 | Li | B01J 23/888 |
| 2010/0298126 | A1* | 11/2010 | De Graaf | B01J 35/613 |
| | | | | 502/201 |
| 2016/0185698 | A1 | 6/2016 | Zhao et al. | |
| 2018/0117579 | A1 | 5/2018 | Scher et al. | |
| 2018/0162785 | A1 | 6/2018 | Liang et al. | |

FOREIGN PATENT DOCUMENTS

| | | |
|---|---|---|
| WO | WO 2014/143880 | 9/2014 |
| WO | WO 2015/101345 | 7/2015 |
| WO | WO 2016/200503 | 12/2016 |
| WO | WO 2016/200504 | 12/2016 |
| WO | WO 2018/164983 | 9/2018 |

OTHER PUBLICATIONS

Arndt, et al., "Mn—$Na_2WO_4$/$SiO_2$ As a Catalyst for the Oxidative Coupling of Methane. What is Really Known?", *Applied Catalysis A: General*, 425-426: 53-61, 2012.

Dedov, et al., "Oxidative Coupling of Methane Catalyzed by Rare Earth Oxides: Unexpected Synergistic Effect of the Oxide Mixtures," *Applied Catalysis A: General*, 245(2): 209-220, 2003.

Fang, et al., "Oxidative Coupling of Methane on W—Mn Catalysts," *Journal of Molecular Catalysis*, 6: 427-433, 1992.

Fang, et al., "Preparation and Characterization of Catalysts for Oxidative Coupling of Methane," *Journal of Molecular Catalysis*, 6: 255-262, 1992.

Gambo, et al., "Recent Advances and Future Prospect in Catalysts for Oxidative Coupling of Methane to Ethylene: A Review," *Journal of Industrial and Engineering Chemistry*, 59(3): 218-229, 2018.

International Search Report and Written Opinion Issued in Corresponding PCT Patent Application No. PCT/IB2019/060439, dated May 12, 2020.

Wu, et al., "La-Promoted $Na_2WO_4$/Mn/$SiO_2$ Catalysts for the Oxidative Conversion of Methane Simultaneously to Ethylene and Carbon Monoxide," *Applied Catalysis A: General*, 323: 126-134, 2007.

Zavyalova, et al., "Statistical Analysis of Past Catalytic Data on Oxidative Methane Coupling for New Insights Into the Composition of High-Performance Catalysts," *Chem Cat Chem*, 3: 1935-1947, 2011.

\* cited by examiner

CATALYST COMPOSITION FOR THE PRODUCTION C₂ HYDROCARBONS FROM METHANE

CROSS REFERENCE TO RELATED APPLICATIONS

This application is a national phase application under 35 U.S.C. § 371 of International Application No. PCT/IB2019/060439 filed Dec. 4, 2019, which claims the benefit of priority of U.S. Provisional Patent Application No. 62/774,885 filed Dec. 4, 2018, all of which are hereby incorporated by reference in their entirety.

FIELD OF INVENTION

The invention relates to the field of catalyst compositions, used for the oxidative coupling of methane (OCM).

BACKGROUND

Ethylene is one of the most important building blocks in the chemical industry and maximizing its production while maintaining desired operating profits through technology advancements is important for all ethylene producers. Keeping such objective in mind, catalyst development for the industrial production of ethylene and other $C_{2+}$ hydrocarbons from methane is an area of research, which has attracted a lot of attention from both industry and academia. Methane is a widely available feedstock having high calorific value, and if oxidatively coupled, in presence of certain methane coupling catalysts, then commercially high value chemicals such as ethylene can be produced sustainably at high production margins. However, ethylene production leads to the formation of ethyne as an inevitable byproduct and is a severe poison for downstream polymerization processes. Separation processes, such as distillation, however does not reduce ethyne concentration to the necessary benign levels while extraction techniques using organic solvents are not economically viable to be applied in all production plants. Alternatively, the majority of ethyne removal is managed by selective hydrogenation, which adds to the operating and capital costs. Another challenge associated with the production of ethylene is the issue of catalyst deactivation which occurs when the catalyst used for oxidative coupling is subjected to high reactor severity, specifically high temperature conditions and gas velocities, which are typically employed in the reactor. Thus, for commercial production of ethylene and other $C_{2+}$ hydrocarbons, it is desirable to have catalyst compositions capable of achieving high selectivity for ethylene and low selectivity for ethyne while retaining catalytic sufficient catalytic stability even when subjected to high temperature and severe reactor conditions. Attempts to develop such catalyst systems have been discussed in various literature publication. One such catalyst system reported to have high stability and excellent selectivity for $C_{2+}$ hydrocarbons, is the catalyst system represented by the general formula Mn—$Na_2WO_4$/$SiO_2$. Arndt et. al in their publication (Applied Catalysis A: General, Volumes 425-426, 28 May 2012, Pages 53-61), provides a general review article such for catalyst systems when used in methane coupling reactions. However, as described in the publication, Mn—$Na_2WO_4$/$SiO_2$ catalyst systems are susceptible to deactivation under certain processing conditions, thereby posing additional plant operation challenges. Wu et. al in their publication (Applied Catalysis A: General, Volume 323, Pages 126-134) describes a lanthanum promoted catalyst having suitable $C_{2+}$ hydrocarbon selectivity. Other published literature such as the published patent WO2015101345A1 (Published: July 2015) or EP3194070A2 (Published: July 2017) describe the use of mixed metal oxides having a specific combination of rare earth metals, suitable for oxidative coupling of methane. Although, the results described in such publications are encouraging in terms of addressing some of the concerns pertaining to the overall $C_{2+}$ hydrocarbon selectivity, none of these publications specifically address the issue of reducing the selectivity of ethyne, produced during the oxidative coupling of methane. As may be appreciated by a person skilled in the art, attempts to increase the overall selectivity for $C_{2+}$ hydrocarbons may come at the cost of increasing the selectivity for all $C_{2+}$ hydrocarbons including ethyne, which is not desirable. In addition, attempts to increase $C_{2+}$ hydrocarbon selectivity may come at the cost of reduced activity rate leading to high amounts of unconverted methane in the product stream, rendering the overall process inefficient and operationally expensive. Further, oxidative coupling processes in general, produces large amounts of carbon dioxide as byproducts due to poor catalyst selectivity thereby reducing overall catalyst efficiency and making oxidative coupling of methane environmentally unsustainable in certain cases. From the foregoing reasons, there remains a need to develop a catalyst composition for the oxidative coupling of methane, having one or more benefits of (i) reduced susceptibility to deactivation under high reactor severity or temperature condition, (ii) having high $C_{2+}$ hydrocarbons selectivity, specifically ethylene, while maintaining low selectivity for ethyne, (iii) retaining sufficient catalytic activity rate for producing $C_{2+}$ hydrocarbon mixture product, and (iv) reduced carbon dioxide selectivity and increased carbon monoxide selectivity.

SUMMARY

The invention relates to a composition comprising a blended product of: (a) a first catalyst component comprising an alkaline earth metal and at least one rare earth element, the first catalyst component having an initial first catalytic activity rate and is present in an amount more than 0 wt. % to about 25 wt. % of the total weight of the composition; and (b) a second catalyst component comprising a transition metal element having redox property and an alkali metal tungstate compound, the second catalyst component having an initial second catalytic activity rate and is present in an amount, greater than about 75 wt. % of the total weight of the composition. Further, the composition has a catalytic activity rate that is more than the initial second catalytic activity rate and less than the initial first catalytic activity rate. In one embodiment of the invention, the composition has a catalytic activity rate ranging from about 5 times to about 60 times of the initial second catalytic activity rate and the initial first catalytic activity rate ranging from about 5 times to about 150 times of the initial second catalytic activity rate. In one embodiment, the first catalyst component is present in an amount ranging from about 4 wt. % to about 15 wt. %, of the total weight of the composition. In one embodiment, the first catalyst component is represented by the general formula (I): $AE_aRE1_bRE2_cAT_dO_x$, wherein (a) 'AE' represents an alkaline earth metal; (b) 'RE1' represents a first rare earth element; (c) 'RE2' represents a second rare earth element; and (d) 'AT' represents a first redox agent or a third rare earth element (RE3); wherein, 'a', 'b', 'c' and 'd' represents relative molar ratio; wherein 'a' is 1; 'b' ranges from about 0.1 to about 10; 'c' ranges from about 0.01 to about 10; 'd' ranges from 0 to about 10; 'x' balances the oxidation state; wherein, the first rare earth element, the second rare earth element and the third rare earth element are different. In one embodiment, the alkaline earth metal is selected from the group consisting of magnesium, calcium, strontium, barium, and combinations thereof. In an another embodiment of the invention, the second catalyst component is represented by the general formula (II): $(M1_e\text{-}TM\text{-}(AM)_2WO_4/SiO_2)$ wherein, (a) 'M1' represents a second redox agent or a fourth rare earth element (RE4) and is present in an amount ranging from 0 wt. % to about 10 wt. %; (b) $(AM)_2WO_4$ represents an alkali metal tungstate selected from the group consisting of lithium tungstate, sodium tungstate, potassium tungstate, rubidium tungstate, caesium tungstate and combinations thereof, and is present in an amount ranging from more than 0 to about 10 wt. %; (c) 'TM' represents a third redox agent and is present in an amount ranging from more than 0 wt. % to about 10 wt. %; (d) 'e' ranges from 0 to about 10. Further, 'M1' and 'TM' are different elements.

In one embodiment of the invention, the first rare earth element, the second rare earth element, the third rare element and the fourth rare element are each independently selected from the group consisting of lanthanum, scandium, cerium, praseodymium, neodymium, promethium, samarium, europium, gadolinium, yttrium, terbium, dysprosium, holmium, erbium, thulium, ytterbium, lutetium, and combinations thereof. In an another embodiment of the invention, the first redox agent, the second redox agent and the third redox agent are each independently selected from the group consisting of manganese, tungsten, bismuth, antimony, tin, cerium, praseodymium, vanadium, chromium, iron, cobalt and combinations thereof. In one embodiment, the alkaline earth metal is selected from the group consisting of magnesium, calcium, strontium, barium, and combinations thereof. In one aspect of the invention, the composition has an ethyne selectivity ranging from more than 0 to 2% of product formed and an ethylene selectivity of at least 42% of product formed when the composition is used in a process that makes $C_{2+}$ hydrocarbon mixture product from methane. In one embodiment of the invention, ethylene selectivity ranges from 42% to 65% of product formed when the composition is used in a process that makes $C_{2+}$ hydrocarbon mixture product from methane. In one embodiment of the invention, the composition has a carbon dioxide selectivity less than 15% of product formed when the composition is used in a process that makes $C_{2+}$ hydrocarbon mixture product from methane. In one embodiment of the invention, the composition has an effective $C_{2+}$ hydrocarbon selectivity ranging from 1% to 10% greater than effective $C_{2+}$ hydrocarbon selectivity of the second catalyst component. In an embodiment of the invention, the composition has a deactivation rate at least 30% slower than the second catalyst component. In one embodiment of the invention, a method for preparing the composition containing the blended product of the first catalyst component and second the catalyst component, is described. The method comprises (a) blending more than 0 wt. % to about 25 wt. % of the first catalyst component with greater than about 75 wt. % of the second catalyst component, and (b) forming the composition. Another aspect of the invention, relates to a composition comprising a $C_{2+}$ hydrocarbon mixture product formed using the composition containing the blended product of the first catalyst component and the second catalyst component. In one aspect of the invention, the $C_{2+}$ hydrocarbon mixture product comprises ethylene, ethane, ethyne, propene, propane, $C_4$-$C_5$ hydrocarbons, carbon dioxide, carbon monoxide and combinations thereof. In one aspect of the invention, a process for producing the $C_{2+}$ hydrocarbon mixture product is described. The process comprises the steps of (a) introducing a feed mixture comprising methane and oxygen in a reactor containing the composition having the blended product of the first catalyst component and the second catalyst component; (b) subjecting the feed mixture to a methane coupling reaction under conditions suitable to produce the $C_{2+}$ hydrocarbon mixture product; and (c) recovering the $C_{2+}$ hydrocarbon mixture product after removing unconverted methane and steam from the $C_{2+}$ hydrocarbon mixture product. In some embodiments of the invention, methane to oxygen ratio ranges from about 2:1 to about 15:1. In embodiments of the invention, the $C_{2+}$ hydrocarbon mixture product is produced at a reactor temperature ranging from about 400° C. to about 900° C. An embodiment of the invention relates to a composition comprising a blended product having: (i) a first catalyst component represented by a general formula (I): $AE_aRE1_bRE2_cAT_dO_x$ wherein, (a) 'AE' represents an alkaline earth metal; (b) 'RE1' represents a first rare earth element; (c) 'RE2' represents a second rare earth element; (d) 'AT' represents a first redox agent or a third rare earth element (RE3); wherein, 'a', 'b', 'c' and 'd' represents relative molar ratio; wherein 'a' is 1; 'b' ranges from about 0.1 to about 10; 'c' ranges from about 0.01 to about 10; 'd' ranges from 0 to about 10; 'x' balances the oxidation state; wherein, the first rare earth element (RE1), the second rare earth element (RE2) and the third rare earth element (RE3) are different; wherein, the first catalyst component has an initial first catalytic activity rate and is present in an amount more than 0 to about 25 wt. % of the composition; and (ii) a second catalyst component represented by a general formula (II): $(M1_e\text{-}TM\text{-}(AM)_2WO_4/SiO_2)$ wherein, (a) 'M1' represents a second redox agent or a fourth rare earth element (RE4) and is present in an amount ranging from 0 wt. % to about 10 wt. %; (b) $(AM)_2WO_4$ represents an alkali metal tungstate selected from the group consisting of lithium tungstate, sodium tungstate, potassium tungstate, rubidium tungstate, caesium tungstate and combinations thereof, and is present in an amount ranging from more than 0 to about 10 wt. %; (c) 'TM' represents a third redox agent and is present in an amount ranging from more than 0 to about 10 wt. %; (d) 'e' ranges from 0 to about 10 and 'M1' and 'TM' are different elements, wherein the second catalyst component has an initial second catalytic activity rate and is present in an amount greater than about 75 wt. % of the composition. Further, the composition has a catalytic activity rate that is more than the initial second catalytic activity rate and less than the initial first catalytic activity rate with the composition having an ethyne selectivity ranging from more than 0 to 2% of product formed, and an ethylene selectivity of at least 42% of product formed, when the composition is used in a process that makes $C_{2+}$ hydrocarbon mixture product from methane.

In the context of the present invention, at least the following embodiments are now described. Embodiment 1 is a composition. The composition contains a blended product of: (a) a first catalyst component comprising an alkaline earth metal and at least one rare earth element, the first catalyst component having an initial first catalytic activity rate and is present in an amount more than 0 wt. % to about 25 wt. % of the total weight of the composition; and (b) a second catalyst component comprising a transition metal element having redox property and an alkali metal tungstate compound, the second catalyst component having an initial second catalytic activity rate and is present in an amount, greater than about 75 wt. % of the total weight of the composition; wherein, the composition has a catalytic activity rate that is more than the initial second catalytic activity rate and less than the initial first catalytic activity rate. Embodiment 2 is the composition of embodiment 1, wherein the composition has a catalytic activity rate ranging from about 5 times to about 60 times of the initial second catalytic activity rate and the initial first catalytic activity rate ranging from about 5 times to about 150 times of the initial second catalytic activity rate. Embodiment 3 is the composition of embodiment 1, wherein the first catalyst component is present in an amount ranging from about 4 wt. % to about 15 wt. %, of the total weight of the composition. Embodiment 4 is the composition of embodiment 1, wherein the first catalyst component is represented by a general formula (I): $AE_aRE1_bRE2_cAT_eO_x$ wherein, (a) 'AE' represents an alkaline earth metal; (b) 'RE1' represents a first rare earth element; (c) 'RE2' represents a second rare earth element; and (d)'AT' represents a first redox agent or a third rare earth element (RE3); wherein, 'a', 'b', 'c' and 'd' represents relative molar ratio; wherein 'a' is 1; 'b' ranges from about 0.1 to about 10; 'c' ranges from about 0.01 to about 10; 'd' ranges from 0 to about 10; 'x' balances the oxidation state; wherein, the first rare earth element, the second rare earth element and the third rare earth element, are different. Embodiment 5 is the composition of embodiment 4, wherein the alkaline earth metal is selected from the group consisting of magnesium, calcium, strontium, barium, and combinations thereof. Embodiment 6 is the composition of embodiment 1, wherein the second catalyst component is represented by a general formula (II): $(M1_e\text{-TM-}(AM)_2WO_4/SiO_2)$ wherein: (a) 'M1' represents a second redox agent or a fourth rare earth element (RE4) and is present in an amount ranging from 0 wt. % to about 10 wt. %; (b) $(AM)_2WO_4$ represents an alkali metal tungstate selected from the group consisting of lithium tungstate, sodium tungstate, potassium tungstate, rubidium tungstate, caesium tungstate and combinations thereof, and is present in an amount ranging from more than 0 wt. % to about 10 wt. %; (c) 'TM' represents a third redox agent and is present in an amount ranging from more than 0 wt. % to about 10 wt. %; (d) 'e' ranges from 0 to about 10; wherein, 'M1' and 'TM' are different elements. Embodiment 7 is the composition of embodiment 4 or 6, wherein the first rare earth element, the second rare earth element, the third rare element and the fourth rare element are each independently selected from the group consisting of lanthanum, scandium, cerium, praseodymium, neodymium, promethium, samarium, europium, gadolinium, yttrium, terbium, dysprosium, holmium, erbium, thulium, ytterbium, lutetium, and combinations thereof. Embodiment 8 is the composition of embodiment 4 or 5, wherein the first redox agent, the second redox agent and the third redox agent are each independently selected from the group consisting of manganese, tungsten, bismuth, antimony, tin, cerium, praseodymium, vanadium, chromium, iron, cobalt and combinations thereof. Embodiment 9 is the composition of embodiment 1, wherein the composition has an ethyne selectivity ranging from more than 0 to 2% of product formed and an ethylene selectivity of at least 42% of product formed, when the composition is used in a process that makes $C_{2+}$ hydrocarbon mixture product from methane. Embodiment 10 is the composition of embodiment 9, wherein ethylene selectivity ranges from 42% to 65% of product formed when the composition is used in a process that makes $C_{2+}$ hydrocarbon mixture product from methane. Embodiment 11 is the composition of embodiment 1, wherein the composition has an effective $C_{2+}$ hydrocarbon selectivity ranging from 1% to 10% greater than effective $C_{2+}$ hydrocarbon selectivity of the second catalyst component. Embodiment 12 is the composition of embodiment 1, wherein the composition has a carbon dioxide selectivity less than 15% of product formed when the composition is used in a process that makes $C_{2+}$ hydrocarbon mixture product from methane. Embodiment 13 is the composition of embodiment 1, wherein the composition has a deactivation rate at least 30% slower than the second catalyst component. Embodiment 14 is a method for preparing the composition of embodiment 1. The method includes the steps of (a) blending more than 0 to about 25 wt. % of the first catalyst component with greater than about 75 wt. % of the second catalyst component, and (b) forming the composition. Embodiment 15 is a composition comprising a $C_{2+}$ hydrocarbon mixture product, wherein the composition is formed using the composition of embodiment 1. Embodiment 16 is the composition of embodiment 15, wherein the $C_{2+}$ hydrocarbon mixture product comprises ethylene, ethane, ethyne, propene, propane, $C_4$-$C_5$ hydrocarbons, carbon dioxide, carbon monoxide and combinations thereof. Embodiment 17 is a process for producing a $C_{2+}$ hydrocarbon mixture product. The process includes the steps of (a) introducing a feed mixture comprising methane and oxygen in a reactor containing the composition of embodiment 1; (b) subjecting the feed mixture to a methane coupling reaction under conditions suitable to produce the $C_{2+}$ hydrocarbon mixture product; and (c) recovering the $C_2$ hydrocarbon mixture product after removing unconverted methane and steam from the $C_{2+}$ hydrocarbon mixture product. Embodiment 18 is the process of embodiment 17, wherein methane to oxygen ratio ranges from about 2:1 to about 15:1. Embodiment 19 is the process of embodiment 17, wherein the $C_{2+}$ hydrocarbon mixture product is produced at a reactor temperature ranging from about 400° C. to about 900° C.

Other objects, features and advantages of the invention will become apparent from the following figures, detailed description, and examples. It should be understood, however, that the figures, detailed description, and examples, while indicating specific embodiments of the invention, are given by way of illustration only and are not meant to be limiting.

DETAILED DESCRIPTION

Figure 1:
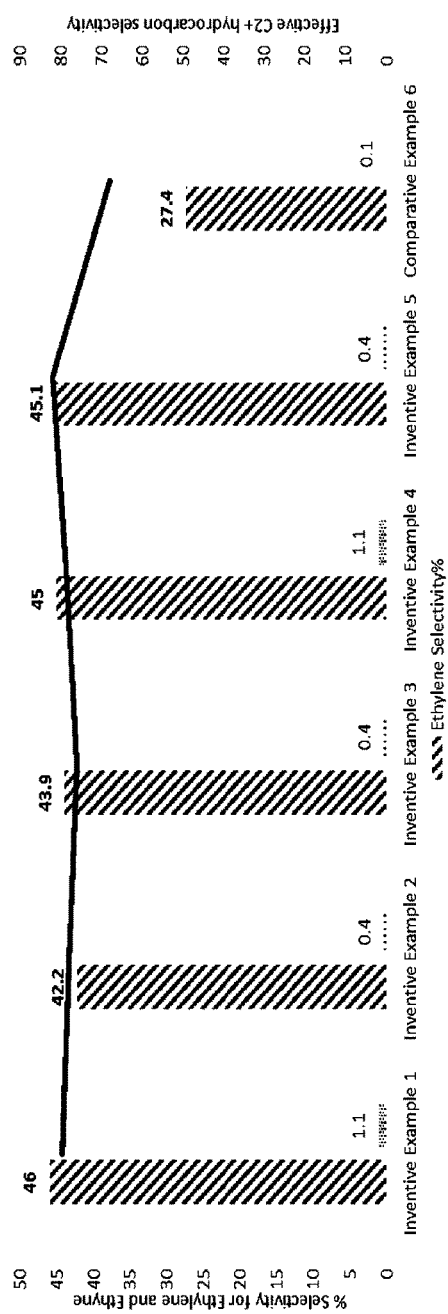
FIG. 1 is a graphical representation of the results obtained from the practice of the inventive examples Example 1-5 along with the results obtained from the practice of comparative example, Example 6.

The invention is based, in part, on the discovery that a composition containing a catalyst, can be used for the oxidative coupling of methane with one or more benefits of (i) reduced susceptibility to deactivation under high reactor severity or temperature condition, (ii) having high $C_{2+}$ hydrocarbons selectivity, specifically ethylene while maintaining low selectivity for ethyne, (iii) retaining sufficient catalytic activity rate for producing $C_{2+}$ hydrocarbon mixture product, and (iv) reduced carbon dioxide selectivity and increased carbon monoxide selectivity. Advantageously, the composition is formulated by synergistically blending two catalyst components, so as to catalyze the coupling reaction between methane and oxygen, to produce a unique composition of $C_{2+}$ hydrocarbon mixture product having high ethylene content and low ethyne content, thereby enabling cost effective recovery of ethylene and other useful hydrocarbon products.

The following includes definitions of various terms and phrases used throughout this specification. The terms "about" or "approximately" or "substantially" are defined as being close to as understood by one of ordinary skill in the art. In one non-limiting embodiment the terms are defined to be within 1%, preferably, within 0.1%, more preferably, within 0.01%, and most preferably, within 0.001%. The terms "wt. %", "vol. %", or "mol. %" refers to a weight, volume, or molar percentage of a component, respectively, based on the total weight, the total volume, or the total moles of material that includes the component. In a non-limiting example, 10 moles of a particular component present in a 100 moles of a material is 10 mol. % of component. The use of the words "a" or "an" when used in conjunction with the term "comprising," "including," "containing," or "having" in the claims or the specification may mean "one," but it is also consistent with the meaning of "one or more," "at least one," and "one or more than one." The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The method of the invention can "comprise," "consist essentially of," or "consist of" particular ingredients, components, compositions, etc., disclosed throughout the specification.

Any numerical range used through this disclosure shall include all values and ranges there between unless specified otherwise. For example, a boiling point range of 50° C. to 100° C. includes all temperatures and ranges between 50° C. and 100° C. including the temperature of 50° C. and 100° C. The term "$C_{2+}$ hydrocarbon" means hydrocarbon products having at least two carbon atoms. The term "initial first catalytic activity rate" and the term "initial second catalytic activity rate" as used in this disclosure means the individual catalytic activity rate of the first catalyst component and the second catalyst component respectively, prior to blending. The term "overall $C_{2+}$ hydrocarbon" or "$C_2$ hydrocarbon mixture product" as used in this disclosure means the hydrocarbon products produced having at least two carbon atoms and includes ethylene, ethane, ethyne, propene, propane, and $C_4$-$C_5$ hydrocarbons. The term "effective $C_{2+}$ hydrocarbon" as used in this disclosure means $C_{2+}$ hydrocarbon excluding ethyne and represents the portion of $C_2$ hydrocarbon mixture product which is commercially viable and indicates the selectivity of the catalyst composition towards the useful hydrocarbon products. The term "redox agent" as used herein means substances or elements capable of undergoing or promoting or supporting both oxidation or reducing reactions. The term "selectivity" to a desired product or products refers to how much desired product was formed divided by the total products formed, both desired and undesired. For purposes of the disclosure herein, the selectivity to a desired product is a % selectivity based on moles converted into the desired product. Further, for purposes of the disclosure herein, a Cx selectivity (e.g., $C_2$ selectivity, $C_{2+}$ selectivity, etc.) can be calculated by dividing a number of moles of carbon (C) from $CH_4$ that were converted into the desired product (e.g., $C_{C2H4}$, $C_{C2H6}$, etc.) by the total number of moles of C from $CH_4$ that were converted (e.g., $C_{C2H4}$, $C_{C2H6}$, $C_{C2H2}$, $C_{C3H6}$, $C_{C3H8}$, $C_{C4S}$, $C_{CO2}$, $C_{CO}$, etc.). $C_{C2H4}$=number of moles of C from $CH_4$ that were converted into $C_2H_4$; $C_{C2H6}$=number of moles of C from $CH_4$ that were converted into $C_2H6$; $C_{C2H2}$=number of moles of C from $CH_4$ that were converted into $C_2H_2$; $C_{C3H6}$=number of moles of C from $CH_4$ that were converted into $C_3H_6$; $C_{C3H8}$=number of moles of C from $CH_4$ that were converted into $C_3H_8$; $C_{C4S}$=number of moles of C from $CH_4$ that were converted into $C_4$ hydrocarbons ($C_{4S}$); $C_{CO2}$=number of moles of C from $CH_4$ that were converted into $CO_2$; $C_{CO}$=number of moles of C from $CH_4$ that were converted into CO; etc. A $C_{2+}$ hydrocarbon selectivity (e.g., selectivity to $C_{2+}$ hydrocarbons) refers to how much $C_2H_4$, $C_3H_6$, $C_2H_2$, $C_2H_6$, $C_3H_8$, $C_{5S}$ and $C_{4S}$ were formed divided by the total products formed, including $C_2H_4$, $C_3H_6$, $C_2H_2$, $C_2H_6$, $C_3H_8$, $C_{4S}$, $C_{5S}$ $CO_2$ and CO.

The invention provides for a composition, containing a catalyst, comprising a blended product of: (a) a first catalyst component comprising an alkaline earth metal and at least one rare earth element, and (b) a second catalyst component comprising a transition metal element having redox property and an alkali metal tungstate compound, in which the first catalyst component and the second catalyst component are blended in a specific proportion that enables the composition to be suitable for catalyzing oxidative coupling of methane and produce $C_{2+}$ hydrocarbon mixture product. In one aspect of the invention, the first catalyst component is present in an amount ranging from more than 0 wt. % to about 25 wt. %, alternatively from about 4 wt. % to about 15 wt. %, alternatively from about 5 wt. % to about 10 wt. % of the total weight of the composition. In an another aspect of the invention, the second catalyst component is present in an amount greater than about 75 wt. %, alternatively in an amount ranging from about 85 wt. % to about 96 wt. %, alternatively in an amount ranging from 90 wt. % to about 95 wt. %, of the total weight of the composition.

In one aspect of the invention, the first catalyst component is represented by a general formula (I): $AE_aRE1_bRE2_cAT_dO_x$, wherein (a) 'AE' represents an alkaline earth metal; (b) 'RE1' represents a first rare earth element; (c) 'RE2' represents a second rare earth element; and (d) 'AT' represents a first redox agent or a third rare earth element (RE3); wherein, 'a', 'b', 'c' and 'd' represents relative molar ratio; wherein 'a' is 1, 'b' ranges from about 0.1 to about 10, alternatively from about 0.3 to about 3, alternatively from about 0.6 to about 2, 'c' ranges from about 0.01 to about 10, alternatively from about 0.07 to about 1, alternatively from about 0.07 to about 0.8, 'd' ranges from 0 to about 10, alternatively from about 0.1 to about 5, and 'x' balances the oxidation state. In an embodiment of the invention, the alkaline earth metal (AE) is selected from the group consisting of magnesium, calcium, strontium, barium, and combinations thereof. In one preferred embodiment of the invention, the alkaline earth metal (AE) is strontium. In one embodiment of the invention, 'AT' is a third rare earth element (RE3). In one embodiment of the invention, the first rare earth element (RE1), the second rare earth element (RE2), the third rare element (RE3) are each independently selected from the group consisting of lanthanum, scandium, cerium, praseodymium, neodymium, promethium, samarium, europium, gadolinium, yttrium, terbium, dysprosium, holmium, erbium, thulium, ytterbium, lutetium, and combinations thereof. In one preferred embodiment of the invention, the first rare earth element (RE1) is lanthanum. In one embodiment of the invention, 'AT' is a first redox agent. The first redox agent is selected from the group consisting of manganese, tungsten, bismuth, antimony, tin, cerium, praseodymium, vanadium, chromium, iron, cobalt and combinations thereof. In one aspect of the invention, the second catalyst component is represented by the general formula (II): $(M1_e\text{-}TM\text{-}(AM)_2WO_4/SiO_2)$ wherein, (a) 'M1' represents a second redox agent or a fourth rare earth element (RE4) and is present in an amount ranging from 0 wt. % to about 10 wt. %, alternatively from 2 wt. % to 8 wt. %, alternatively from 4 wt. % to 6 wt. %; (b) $(AM)_2WO_4$ represents an alkali metal tungstate selected from the group consisting of lithium tungstate, sodium tungstate, potassium tungstate, rubidium tungstate, caesium tungstate and combinations thereof, and is present in an amount ranging from more than 0 to about 10 wt. %, alternatively from 2 wt. % to 8 wt. %, alternatively from 3 wt. % to 6 wt. %; (c) 'TM' represents a third redox element and is present in an amount ranging from more than 0 to about 10 wt. %, alternatively from 1 wt. % to about 6 wt. %, alternatively from 2 wt. % to 4 wt. %; (d) 'e' ranges from 0 to about 10. In one embodiment of the invention, 'M1' and 'TM' are different elements. The second redox agent and the third redox agent are each independently selected from the group consisting of manganese, tungsten, bismuth, antimony, tin, cerium, praseodymium, vanadium, chromium, iron, cobalt and combinations thereof. In one preferred embodiment, the third redox agent is manganese (Mn). In one embodiment of the invention, 'M1' is a fourth rare earth element (RE4). The fourth rare earth element (RE4) is selected from the group consisting of lanthanum, scandium, cerium, praseodymium, neodymium, promethium, samarium, europium, gadolinium, yttrium, terbium, dysprosium, holmium, erbium, thulium, ytterbium, lutetium, and combinations thereof. In one embodiment of the invention, 'M1' is a second redox agent. Without wishing to be bound by any specific theory, 'M1' functions as a promoter for the second catalyst component, and aids in enhancing the performance of the catalyst component. As reported by Arndt et. al, the silica ($SiO_2$) functions as a support and may undergo phase transition to form a more inert crystalline alpha-cristobalite structure, which regulates the stability and selectivity of the second catalyst component during the course of the catalysis. In one aspect of the invention, a method for preparing the composition containing the blended product of the first catalyst component and the second catalyst component comprises (a) blending more than 0 wt. % to about 25 wt. %, alternatively from about 4 wt. % to about 15 wt. %, alternatively from about 5 wt. % to about 10 wt. %, of the first catalyst component, with greater than about 75 wt. %, alternatively from about 85 wt. % to about 96 wt. %, alternatively from about 90 wt. % to about 95 wt. % of the second catalyst component, and (b) forming the composition. In one embodiment of the invention, the method further comprises grinding and press sizing the composition. In one aspect of the invention, the method further comprises forming the composition to special shape for loading into reactors.

The first catalyst component can be prepared by a method involving the step of forming an aqueous catalyst precursor solution containing a mixture of (i) a compound containing the alkaline earth metal (AE), (ii) a compound containing the first rare earth element (RE1) (iii) a compound containing the second rare earth metal (RE2) and (iv) a compound containing the third rare earth metal (RE3) or the first redox agent. Subsequently, the aqueous catalyst precursor solution can be dried and thereafter calcined to obtain the first catalyst component. The drying step can be carried out at a temperature ranging from about 90° C. to about 150° C., alternatively at a temperature ranging from about 110° C. to about 140° C., alternatively at a temperature ranging from about 115° C. to about 130° C. The calcination step can be carried out at a temperature ranging from about 700° C. to about 950° C., alternatively from about 750° C. to about 900° C., for at least 5 hours. Non-limiting examples of compounds used as a precursor material for the catalyst preparation containing the alkaline earth metal (AE), first rare earth element (RE1), second rare earth element (RE2), third rare earth element (RE3), first redox agent, are nitrates, carbonates, acetates, halides, oxides, hydroxides and any combinations thereof.

The second catalyst component can be prepared by either of two methods a) incipient wetness method or impregnation method involving the use of silica gel, or by b) slurry preparation method involving the use of silica sol. The incipient wetness method involves the step of forming an impregnated silica gel by impregnating a dried silica gel material with an aqueous solution containing the third redox agent. Subsequently, an aqueous solution containing the alkali metal tungstate, is added to the impregnated silica gel to form an aqueous catalyst precursor solution. Optionally, a compound containing the second redox agent or the fourth rare earth element (RE4) may be blended with the impregnated silica gel prior to adding the solution containing the alkali metal tungstate compound. The aqueous catalyst precursor solution is subsequently dried overnight and thereafter calcined for at least 5 hours to obtain the second catalyst component. In certain embodiments, the aqueous catalyst precursor may be agitated at a temperature of at least 80° C., alternatively at least 90° C. prior to initiating the drying step. The drying step can be carried out at a temperature ranging from about 90° C. to about 150° C., alternatively at a temperature ranging from about 110° C. to about 140° C., alternatively at a temperature ranging from about 115° C. to about 130° C. The calcination step can be carried out at a temperature ranging from about 700° C. to about 950° C., alternatively from about 750° C. to about 850° C. Alternatively, the second catalyst component may be prepared by the slurry preparation method involving the use of silica sol having a silica content of 10%-50%, to which an aqueous solution containing the third redox agent is added to form a silica sol slurry. Subsequently, an aqueous solution containing the alkali metal tungstate may be added to the silica sol slurry to form a catalyst precursor. Optionally, a compound containing the second redox agent or the fourth rare earth element (RE4) may be added to the slurry prior to adding the solution containing the alkali metal tungstate. The catalyst precursor may be dried and calcined under same conditions as described for the incipient wetness method to form the second catalyst component. Non-limiting examples of compounds that can be used as a precursor compounds for preparing the second catalyst component can be are nitrates, carbonates, acetates, halides, oxides, hydroxides and any combinations thereof.

In one aspect of the invention, a process for producing a $C_{2+}$ hydrocarbon mixture product, using the composition containing the blended product of the first catalyst component and the second catalyst component is provided. The process comprises (a) introducing a feed mixture comprising methane and oxygen in a reactor containing the composition comprising the blended product of the first catalyst component and the second catalyst component (b) subjecting the feed mixture to a methane coupling reaction under conditions suitable to produce the $C_{2+}$ hydrocarbon mixture product and (c) recovering the $C_{2+}$ hydrocarbon mixture product after removing unconverted methane and steam from the $C_{2+}$ hydrocarbon mixture product. In one embodiment of the invention, the removal of unconverted methane and steam from the $C_{2+}$ hydrocarbon mixture product is effected using a distillation column. In one embodiment the distillation column is a cryogenic distillation column. In one embodiment of the invention, the feed mixture comprising methane and oxygen may be preheated to a temperature ranging from about 400° C. to about 550° C., alternatively from about 450° C. to about 500° C., prior to introducing the feed mixture in the reactor for methane coupling. The reactor can comprise an adiabatic reactor, an autothermal reactor, an isothermal reactor, a tubular reactor, a cooled tubular reactor, a continuous flow reactor, a fixed bed reactor, a fluidized bed reactor, a moving bed reactor, and the like, or combinations thereof. In an aspect, the reactor can comprise an adiabatic reactor. In one aspect of the invention, the $C_2$ hydrocarbon mixture product is produced at a reactor temperature ranging from about 400° C. to about 900° C., alternatively from about 600° C. to about 850° C., alternatively from about 700° C. to about 810° C. In an aspect, the reactor can comprise a catalyst bed comprising the composition capable of catalyzing the oxidative coupling of methane. In one embodiment of the invention, the ratio of methane to oxygen ratio ranges from about 2:1 to about 15:1, alternatively from about 4:1 to about 10:1, alternatively from about 5:1 to about 8:1. Advantageously, the inventive catalyst composition of the present invention is able to operate and retain its activity even when subjected to high methane to oxygen ratio without deterioration of catalyst performance. In one embodiment of the invention, the pressure in the reactor is maintained at a pressure sufficient to effect oxidative coupling of methane. The pressure may be maintained at a range of about 14.7 psi (ambient atmospheric pressure) to about 500 psi. In one embodiment, the feed mixture is introduced into the reactor at a gas hourly space velocity (GHSV) ranging from about 500 h$^{-1}$ to about 1,000,000 h$^{-1}$, alternatively from about 1,000 h$^{-1}$ to about 300,000 h$^{-1}$, alternatively from about 5,000 h$^{-1}$ to about 100,000 h$^{-1}$, alternatively from about 10,000 h$^{-1}$ to about 80,000 h$^{-1}$, alternatively from about 20,000 h$^{-1}$ to about 50,000 h$^{-1}$. In one aspect of the invention, the composition has a deactivation rate at least 30%, alternatively at least 60%, alternatively at least 75%, alternatively of at least 90%, slower than the second catalyst component. The term "slower" as used herein means that the catalyst is able to retain oxygen conversion of at least 98% for a longer period of time on stream in the reactor before deactivation. Thus, it may be concluded that the composition comprising the blended product of the first catalyst component and the second catalyst component is stable and is able to retain high oxygen conversion even under high reactor severity and under high temperature conditions. Based on the selectivity data from Table 19 of this disclosure, it is evident that the inventive catalyst composition demonstrates high selectivity towards ethylene and other useful $C_2$-$C_5$ hydrocarbon products. The selectivity property exhibited by the inventive catalyst composition, results in lowering of the overall heat produced during the coupling reaction, thereby improving catalyst performance and also aiding in controlling reactor operations.

The composition containing the blended product of the first catalyst component and the second catalyst component provides the composition with a synergistic combination of catalytic activity rate derived from the blending of the first catalyst component and the second catalyst components at a specific proportion. Particularly, the inventive composition demonstrates significant improvement in the catalytic activity rate when compared to the constituent second catalyst component. In one aspect of the invention, the first catalyst component having an initial first catalytic activity rate when blended with the second catalyst component having an initial second catalytic activity rate, produces the composition with a catalytic activity rate that is more than the initial second catalytic activity rate and less than the initial first catalytic activity rate. The catalytic activity rate as measured for the purpose of this invention is the relative catalytic activity rate in comparison to the catalytic activity rate of the second catalyst component. In an embodiment of the invention, the initial first catalytic activity rate ranges from about 5 times to about 150 times, alternatively from about 40 times to about 110 times, alternatively from about 60 times to about 90 times, of the initial second catalytic activity rate. In an embodiment of the invention, the composition containing the blended product of the first catalyst component and the second catalyst component, has a catalytic activity rate ranging from about 5 times to about 60 times, alternatively from about 8 times to about 60 times, alternatively from about 15 times to about 48 times, of the initial second catalytic activity rate. The catalytic activity rate for the composition, for the first catalyst component and the second catalyst component can be selected from any of the values from the ranges described above which satisfy the equation: (SCAR)<(CA)<(FCAR), where, SCAR is the initial second catalytic activity rate of the second catalyst component, CA is the catalytic activity rate of the composition containing the blended product of first catalyst component and second catalyst component, FCAR is the initial first catalytic activity rate of the first catalyst component. Without wishing to be bound by any specific theory, the synergistic effect of the catalyst activity rate is particularly beneficial in obtaining higher content of useful $C_{2+}$ hydrocarbon products, particularly ethylene, with excellent selectivity. The catalytic activity rate is proportional to the rate of oxygen conversion at a specific temperature and can be determined using a gas chromatograph and the catalytic activity rate is calculated using the rate constant of the oxygen conversion reaction. For the purpose of this invention, the oxygen conversion rate can be measured by comparing the oxygen concentration at the inlet of the reactor and the oxygen concentration obtained at a specific reactor temperature, for example, 700° C. during the course of the reaction. The improved catalytic activity rate of the inventive composition allows the conversion to take place at a relatively lower temperature and requiring lower catalyst loading.

In one aspect of the invention, a composition comprising a $C_{2+}$ hydrocarbon mixture product is formed using the composition containing the blended product of the first catalyst component and the second catalyst component. In one aspect of the invention, unconverted methane, and steam is removed from the $C_{2+}$ hydrocarbon mixture product. The composition comprising the $C_{2+}$ hydrocarbon mixture product has a unique blend of high ethylene content with low ethyne content. In an another aspect of the invention, the composition containing the blended product of the first catalyst component and the second catalyst component has an ethyne selectivity ranging from about greater than 0 to 2%, alternatively from 0.2% to 1.8%, alternatively from 0.5% to 1.2%, of product formed when the composition is used in a process that makes $C_2$ hydrocarbon mixture product from methane and an ethylene selectivity of at least 42%, alternatively from 42% to 65%, alternatively from 35% to 48%, of product formed when the composition is used in a process that makes $C_{2+}$ hydrocarbon mixture product s from methane. In one aspect of the invention, the composition containing the blended product of the first catalyst component and the second catalyst component has an overall $C_{2+}$ hydrocarbon selectivity ranging from 70% to 90%, alternatively ranging from 76% to 84%, alternatively ranging from 78% to 83%, of product formed when the composition is used in a process that makes $C_{2+}$ hydrocarbon mixture product from methane. In one embodiment of the invention, the composition has an effective $C_{2+}$ hydrocarbon selectivity ranging from 70% to 90%, alternatively from 72% to 85%, alternatively from 75% to 82%. In one aspect of the invention, the composition has an effective $C_{2+}$ hydrocarbon selectivity ranging from 1% to 10%, alternatively from 1.1% to 6%, alternatively from 2% to 4%, greater than effective $C_{2+}$ hydrocarbon selectivity of the second catalyst component. In one aspect of the invention, the composition has an effective $C_{2+}$ hydrocarbon selectivity ranging from 1% to 15%, alternatively from 1.1% to 10%, alternatively from 2% to 8%, greater than effective $C_{2+}$ hydrocarbon selectivity of the first catalyst component. The improved effective $C_{2+}$ hydrocarbon selectivity of the inventive catalyst composition allows the inventive catalyst composition to be suitable for producing industrially useful, non-ethyne $C_{2+}$ hydrocarbon products with high selectivity. In one aspect of the invention, the composition containing the blended product of the first catalyst component and the second catalyst component has improved carbon monoxide selectivity while retaining a lower carbon dioxide selectivity. In one embodiment of the invention, the composition has a carbon dioxide selectivity less than 15%, alternatively less than 10%, alternatively less than 5%, of product formed when the composition is used in a process that makes $C_{2+}$ hydrocarbon mixture product from methane. This is particularly useful as carbon monoxide produced can be reconverted to useful $C_{2+}$ hydrocarbon products while carbon dioxide cannot be, thus making the catalyst more efficient in terms of carbon conversion efficiency and the catalyst makes the overall oxidative coupling process more sustainable.

Accordingly, the invention includes embodiments that include compositions containing catalysts, that exhibits one or more benefits of (i) reduced susceptibility to deactivation under high reactor severity or temperature condition, (ii) having high $C_{2+}$ hydrocarbon selectivity, specifically ethylene while maintaining low selectivity for ethyne, (iii) retaining sufficient catalytic activity rate for producing $C_{2+}$ hydrocarbon mixture product, and (iv) reduced carbon dioxide selectivity and increased carbon monoxide selectivity. Advantageously, the invention now enables artisans to formulate compositions in such a manner so as to catalyze the coupling reaction between methane and oxygen to produce a unique composition of $C_2$ hydrocarbon mixture product having high ethylene content and low ethyne content, thereby enabling cost effective recovery of ethylene recovery.

Specific examples demonstrating some of the embodiments of the invention are included below. The examples are for illustrative purposes only and are not intended to limit the invention. Those of ordinary skill in the art will readily recognize parameters that can be changed or modified to yield essentially the same results.

EXAMPLES

Example 1 Catalyst Composition Having the Formula $(Sr_1La_{0.9}Nd_{0.7}Yb_{0.1}O_x)_{0.05}$—$(Mn-Na_2WO_4/SiO_2)_{0.95}$ with First Catalyst Component Present in an Amount of 5 wt. % and the Second Catalyst Component Present in an Amount of 95 wt. %

Purpose: Example 1 demonstrates the preparation and use of a composition comprising a catalyst, having the formula $(Sr_1La_{0.9}Nd_{0.7}Yb_{0.1}O_x)_{0.05}$—$(Mn-Na_2WO_4/SiO_2)_{0.95}$. The composition was used for the production of $C_{2+}$ hydrocarbon mixture product with sufficient catalytic activity rate and excellent selectivity, forming mixtures having high ethylene content with limited ethyne content.

Materials: The following materials are procured and used for the synthesis of the composition.

TABLE 1

Material Used (First Catalyst component: $Sr_1La_{0.9}Nd_{0.7}Yb_{0.1}O_x$)

| First catalyst component: $AE_aRE1_bRE2_cRE3_dO_x$ | Element used | Relative molar ratio | Precursor Material | Supplier |
|---|---|---|---|---|
| AE | Strontium (Sr) | a = 1 | Strontium Nitrate: $Sr(NO_3)_2$ | Sigma-Aldrich |
| RE1 | Lanthanum (La) | b = 0.9 | Lanthanum Nitrate $La(NO_3)_3$ | Sigma-Aldrich |
| RE2 | Neodymium (Nd) | c = 0.7 | Neodymium Nitrate: $Nd(NO_3)_3$ | Sigma-Aldrich |
| RE3 | Ytterbium (Yb) | d = 0.1 | Ytterbium Nitrate $Yb(NO_3)_3$ | Sigma-Aldrich |

TABLE 2

Material Used (Second Catalyst component: Mn—Na$_2$WO$_4$/SiO$_2$

| Second catalyst component: (M1$_e$-TM$_1$-(AM)$_2$WO$_4$/SiO$_2$) | Material used | Weight content (%) | Precursor Material | Supplier |
|---|---|---|---|---|
| M1 | NA (e = 0) | — | | |
| Silica | Silica gel | — | (Davisil Grade 646) | Sigma-Aldrich |
| TM | Manganese (Mn) | 1.9 | Manganese Nitrate Mn(NO$_3$)$_2$•4H$_2$O | Sigma-Aldrich |
| (AM)$_2$WO$_4$ | Sodium Tungstate (Na$_2$WO$_4$) | 5.0 | Na$_2$WO$_4$•4H$_2$0 | Sigma-Aldrich |

Method for preparing the composition containing the catalyst of Example 1: The composition was prepared by the method of (a) blending the first catalyst component in an amount more than 0 wt % to about 25 wt % with the second catalyst component in an amount greater than about 75 wt %, and (b) forming the composition. The method further included the step of grinding and press sizing the composition. More particularly, the method included the step of blending 0.5 g of the first catalyst component (Sr$_1$La$_{0.9}$Nd$_{0.7}$Yb$_{0.1}$O$_x$) with 9.5 g of the second catalyst component (Mn—Na$_2$WO$_4$/SiO$_2$) followed by grinding and press sizing the resulting blend. The individual catalyst components, the first catalyst component and the second catalyst component were prepared as given: Method for Preparing the first catalyst component (Sr$_1$La$_{0.9}$Nd$_{0.7}$Yb$_{0.1}$O$_x$) of Example 1: The follow steps were followed for the synthesis of the first catalyst component 10.58 g of Sr(NO$_3$)$_2$, 19.48 g of La(NO$_3$)$_3$·6H$_2$O, 15.35 g of Nd(NO$_3$)$_3$·6H$_2$O and 2.26 g of Yb(NO$_3$)$_3$·5H$_2$O were mixed and dissolved 100 ml water. The resulting material was dried overnight at a temperature of 125° C. and then calcined at a temperature of 900° C. for 6 hours under airflow and the first catalyst component Sr$_1$La$_{0.9}$Nd$_{0.7}$Yb$_{0.1}$O$_x$ was obtained. Method for preparing the second catalyst component (Mn—Na$_2$WO$_4$/SiO$_2$) of Example 1: Incipient wetness method is used for the second catalyst component. Silica gel (18.6 g Davisil Grade 646) was used after drying overnight. Mn(NO$_3$)$_2$·4H$_2$O (1.73 g) was dissolved in deionized water (18.5 ml) and then added dropwise onto the silica gel. The resulting manganese impregnated silica material was dried overnight. Na$_2$WO$_4$·2H$_2$O (1.22 g) was dissolved in deionized water (18.5 ml) and the solution obtained was added onto the dried manganese impregnated silica material obtained from the above step. The resulting material was dried overnight at a temperature of 125° C. and then calcined at a temperature of 800° C. for 6 hours under airflow and the second catalyst component Mn—Na$_2$WO$_4$/SiO$_2$ was obtained with the active component loadings shown in Table 2.

Process for producing C$_{2+}$ hydrocarbon mixture product using the composition of Example 1: The composition obtained from the practice of Example 1 was used for producing C$_{2+}$ hydrocarbon mixture product using the process comprising (a) introducing a feed mixture comprising methane and oxygen in a reactor containing the composition of Example 1; thereafter (b) subjecting the feed mixture to a methane coupling reaction under conditions suitable to produce the C$_{2+}$ hydrocarbon mixture product and subsequently, (c) recovering the C$_{2+}$ hydrocarbon mixture product after removing any unconverted methane and steam. More particularly, the composition containing the catalyst obtained from Example 1, was placed in a 2.3 mm ID quartz tube, and was contacted with a feed mixture containing methane and oxygen. The ratio of methane to oxygen was adjusted to a ratio of 7.4:1 and the feed mixture flow rate was adjusted from 40 sccm. The catalyst loading in the reactor was 20 mg. The reactors were operated under ambient pressure. Under different reactor temperatures, catalyst performance was obtained. Products obtained were analyzed using online Gas Chromatograph having a thermal conductivity detector (TCD) and a flame ionization detector (FID).

The operating parameters for producing the C$_{2+}$ hydrocarbon mixture product as given below:

TABLE 3

Operating Parameter used for producing C$_{2+}$ hydrocarbon mixture product

| Start reactor temperature of testing (° C.) | End reactor temperature of testing (° C.) | Pressure inside reactor (psi) | Gas Hourly Space Velocity (GHSV) (hr$^{-1}$) |
|---|---|---|---|
| 600° C. | 850° C. | Ambient pressure, (14.7) | 57800 |

For the purpose of evaluating the composition comprising the catalyst of Example 1, the individual catalyst components were also tested for their efficacy in producing the C$_{2+}$ hydrocarbon mixture product. The first catalyst component (Sr$_1$La$_{0.9}$Nd$_{0.7}$Yb$_{0.1}$O$_x$) and the second catalyst component (Mn—Na$_2$WO$_4$/SiO$_2$) were each independently subjected to the same reaction condition and process steps as that of the composition of Example 1 ((Sr$_1$La$_{0.9}$Nd$_{0.7}$Yb$_{0.1}$O$_x$)$_{0.05}$—(Mn—Na$_2$WO$_4$/SiO$_2$)$_{0.95}$). For the second catalyst component, due to its low activity, more catalyst (100 mg) was loaded in the reactor to get meaningful results. To avoid reactor pressure, a 4.0 mm quartz tube reactor was used for testing of 100 mg catalyst loading.

Results: The performances obtained using the composition containing catalyst of Example 1 ((Sr$_1$La$_{0.9}$Nd$_{0.7}$Yb$_{0.1}$O$_x$)$_{0.05}$—(Mn—Na$_2$WO$_4$/SiO$_2$)$_{0.95}$) and that obtained from the use of the constituent first catalyst component (Sr$_1$La$_{0.9}$Nd$_{0.7}$Yb$_{0.1}$O$_x$) and the second catalyst component (Mn—Na$_2$WO$_4$/SiO$_2$) are tabulated below:

TABLE 4

Relative catalytic activity rate

| | Catalytic activity rate Example 1 $((Sr_1La_{0.9}Nd_{0.7}Yb_{0.1}O_x)_{0.05}$—$(Mn$—$Na_2WO_4/SiO_2)_{0.95})$ | Initial First Catalyst Component $(Sn_1La_{0.9}Nd_{0.7}Yb_{0.1}O_x)$ | Initial Second Catalyst Component $(Mn$—$Na_2WO_4/SiO_2)$ |
|---|---|---|---|
| Relative Catalytic Activity Rate | 5.9 | 105 | 1.0 |

TABLE 5

Catalyst selectivity/Product composition

| | (Inventive) Example 1 $((Sr_1La_{0.9}Nd_{0.7}Yb_{0.1}O_x)_{0.05}$—$(Mn$—$Na_2WO_4/SiO_2)_{0.95})$ | First Catalyst Component $(Sr_1La_{0.9}Nd_{0.7}Yb_{0.1}O_x)$ | Second Catalyst Component $(Mn$—$Na_2WO_4/SiO_2)$ |
|---|---|---|---|
| Overall $C_{2+}$ hydrocarbon selectivity (%) | 80.8 | 74.4 | 79.7 |
| Ethyne selectivity (%) | 1.1 | 0.3 | 4.4 |
| Effective $C_{2+}$ hydrocarbon selectivity (%) | 79.7 | 74.1 | 75.3 |
| Ethylene selectivity (%) | 46.0 | 37.5 | 46.9 |
| Carbon monoxide selectivity (%) | 10.5 | 3.6 | 10.5 |
| Carbon dioxide selectivity (%) | 8.7 | 22.0 | 9.8 |

The results from Table 4 indicate that the catalytic activity rate of the composition containing the catalyst of Example 1, has a higher catalytic activity rate (5.9) than the second catalyst component (1.0) but a lower catalytic activity rate than the first catalyst component (105.0). In other words, it is evident that catalytic activity rate of the composition is 5.9 times the initial second catalytic activity rate while the initial first catalytic activity rate is 105 times the initial second catalytic activity rate. From Table 5, the results demonstrate a balance of high ethylene selectivity with low ethyne selectivity as compared to that of the individual components constituent the composition of Example 1. Particularly, it is observed that the effective $C_{2+}$ hydrocarbon selectivity is higher compared to the effective $C_{2+}$ hydrocarbon selectivity from obtained from the individual components. It is also observed that the inventive catalyst obtained from the practice of Example 1, demonstrates improved carbon monoxide selectivity while keeping carbon dioxide selectivity low. This is particularly advantageous as carbon monoxide can be reconverted back to more useful chemical products while mitigating the extent of carbon dioxide production thereby reducing green-house gas emission. Thus, it may be concluded that the composition obtained by blending the first catalyst component and the second catalyst component, in the proportion practiced under Example 1, results in a catalyst having sufficient catalytic activity rate with improved (high) ethylene selectivity and low ethyne selectivity while maintaining an overall high $C_{2+}$ hydrocarbon selectivity and ensuring improved sustainability from an environmental stand point.

Example 2 (Variant of the Example 1)—Catalyst Composition Having the Formula $(Sr_1La_{0.9}Nd_{0.7}Yb_{0.1}O_x)_{0.05}$—$(Mn$—$Na_2WO_4 SiO_2)_{0.95}$ with First Catalyst Component Present in an Amount of 5 wt. % and the Second Catalyst Component at 95 wt. %

Purpose: Example 2 has a similar purpose as Example 1, and demonstrates the preparation and use of a composition comprising a catalyst having the formula $(Sr_1La_{0.9}Nd_{0.7}Yb_{0.1}O_x)_{0.05}$—$(Mn$—$Na_2WO/SiO_2)_{0.95}$. The composition obtained from the practice of Example 2 differs from that of Example 1, by way of preparing the constituent second catalyst component involving the use of silica sol with 34% of silica content. Since silica sol is used for preparation of the second catalyst component, slurry preparation method was used for this example.

Materials: The material used was same as reported under Example 1 except that a silica sol with 34% of silica content was used for preparing the second catalyst component.

Method for preparing the composition containing the catalyst of Example 2: The composition containing the blended product of the first catalyst component and the second catalyst component was prepared in the same method as described under Example 1, involving the step of blending 0.5 g of the first catalyst component ($Sr_1La_{0.9}Nd_{0.7}Yb_{0.1}O_x$) with 9.5 g of the second catalyst component (Mn—$Na_2WO_4/SiO_2$) followed by grinding and press sizing the resulting blend. The first catalyst component and the second catalyst component were prepared as given: Method for preparing the first catalyst component ($Sr_1La_{0.9}Nd_{0.7}Yb_{0.1}O_x$) of Example 2: The first catalyst component of Example 2 was prepared in the same manner as described for the first catalyst component of Example 1. Method for preparing the second catalyst component (Mn—$Na_2WO_4/SiO_2$) of Example 2: Slurry preparation method was used for this second catalyst component. 1.74 g of $Mn(NO_3)_2 \cdot 4H_2O$ was dissolved in 15 ml of deionized water and solution obtain was then added to a 28.61 g of silica sol, having silica content of 34%. 1.12 g of $Na_2WO_4 \cdot 2H_2O$ was dissolved in 10 ml of deionized water and the solution obtained was mixed with the silica sol slurry obtained from the above step. Another 50 ml water was added to the mixture and agitated at 90° C. for 2 hours. The resulting material was dried overnight at a temperature of 125° C. and then calcined at a temperature of 800° C. for 6 hours under airflow and the second catalyst component Mn—$Na_2WO_4/SiO_2$ was obtained. The weight content of manganese (Mn) was found to be 3.4 wt. % and the weight content of sodium tungstate ($Na_2WO_4$) was found to be 9.0 wt. %.

Process for producing $C_2$ hydrocarbon mixture product using the composition of Example 2: The composition obtained from the practice of Example 2 was used for producing $C_{2+}$ hydrocarbon mixture product using the process and conditions as described under Example 1. The operating parameters for producing the $C_{2+}$ hydrocarbon mixture product was same as that practiced under Example 1. As shown under Example 1, for the purpose of evaluating the composition comprising the catalyst of Example 2, the individual catalyst components were also tested for their efficacy in producing the $C_{2+}$ hydrocarbon mixture product. The first catalyst component ($Sr_1La_{0.9}Nd_{0.7}Yb_{0.1}O_x$) and the second catalyst component (Mn—$Na_2WO_4/SiO_2$) were each independently subjected to the same reaction condition and process steps as that of the composition of Example 2 (($Sr_1La_{0.9}Nd_{0.7}Yb_{0.1}O_x)_{0.05}$—(Mn—$Na_2WO_4/SiO_2)_{0.95}$). The evaluation of the individual components were carried out using the same procedure practiced for Example 1.

Results: The $C_{2+}$ hydrocarbon mixture product obtained using the composition containing catalyst of Example 2 (($Sr_1La_{0.9}Nd_{0.7}Yb_{0.1}O_x)_{0.05}$—(Mn—$Na_2WO_4/SiO_2)_{0.95}$) and that obtained from the use of the constituent first catalyst component ($Sr_1La_{0.9}Nd_{0.7}Yb_{0.1}O_x$) and the constituent second catalyst component (Mn—$Na_2WO_4/SiO_2$) was analyzed using online Gas Chromatograph having a thermal conductivity detector (TCD) and a flame ionization detector (FID). The results obtained are tabulated below:

TABLE 6

Relative catalytic activity rate

| | (Inventive) Example 2 (($Sr_1La_{0.9}Nd_{0.7}Yb_{0.1}O_x)_{0.05}$—(Mn—$Na_2WO_4/SiO_2)_{0.95}$) | Initial First Catalyst Component ($Sr_1La_{0.9}Nd_{0.7}Yb_{0.1}O_x$) | Initial Second Catalyst Component (Mn—$Na_2WO_4/SiO_2$) |
|---|---|---|---|
| Relative Catalytic Activity Rate | 58.5 | 147.8 | 1.0 |

TABLE 7

Catalyst selectivity/Product composition

| | (Inventive) Example 2 (($Sr_1La_{0.9}Nd_{0.7}Yb_{0.1}O_x)_{0.05}$—(Mn—$Na_2WO_4/SiO_2)_{0.95}$) | First Catalyst Component ($Sr_1La_{0.9}Nd_{0.7}Yb_{0.1}O_x$) | Second Catalyst Component (Mn—$Na_2WO_4/SiO_2$) |
|---|---|---|---|
| Overall $C_{2+}$ hydrocarbon selectivity (%) | 78.5 | 74.4 | 80.2 |
| Ethyne selectivity (%) | 0.4 | 0.3 | 3.6 |
| Effective $C_{2+}$ hydrocarbon selectivity (%) | 78.1 | 74.1 | 76.6 |
| Ethylene selectivity (%) | 42.2 | 37.5 | 47.3 |
| Carbon monoxide selectivity (%) | 9.5 | 3.6 | 7.7 |
| Carbon dioxide selectivity (%) | 12.0 | 22.0 | 12.0 |

The results from Table 7 indicate that compared to Example 1, the composition obtained from Example 2 shows marginally lower selectivity for ethylene as compared to Example 1. However, as desired, the selectivity for ethyne is nearly 36% lower compared to that of the composition from Example 1. As observed, the catalytic activity rate of the composition comprising the catalyst of Example 2, has a higher catalytic activity rate (58.5) than the second catalyst component (1.0) but a lower catalytic activity rate than the first catalyst component (147.8). As shown from the results, the inventive composition of Example 2, demonstrates a balance of high ethylene selectivity with low ethyne selectivity as compared to that of the constituent individual components of Example 2. Particularly, it is observed that the effective $C_{2+}$ hydrocarbon selectivity is higher compared to the effective $C_{2+}$ hydrocarbon selectivity obtained from the individual components. It is also observed that the inventive catalyst obtained from the practice of Example 2, demonstrates improved carbon monoxide selectivity while keeping carbon dioxide selectivity low. This is particularly advantageous as carbon monoxide can be reconverted back to more useful chemical products while mitigating the extent of carbon dioxide production thereby reducing green-house gas emission.

Example 3—Catalyst Composition Having the Formula $(Sr_1La_{0.9}Nd_{0.7}Yb_{0.1}O_x)_{0.1}$—$(Mn$—$Na_2WO_4/SiO_2)_{0.9}$ with First Catalyst Component Present in an Amount of 10 wt. % and the Second Catalyst Component at 90 wt. %

Purpose: Example 3 demonstrates the preparation and use of a composition comprising a catalyst having the formula $(Sr_1La_{0.9}Nd_{0.7}Yb_{0.1}O_x)_{0.1}$—$(Mn$—$Na_2WO_4/SiO_2)_{0.9}$.

Materials: The material used is same as that described under Example 1.

Method for preparing the composition containing the catalyst of Example 3: The process practiced was same as that described under Example 1 except that 1 g of $Sr_1La_{0.9}Nd_{0.7}Yb_{0.1}O_x$ was blended with 9 g of $Mn$—$Na_2WO_4/SiO_2$ to form the composition. The first catalyst component and the second catalyst component, were prepared using the same method as that described under Example 1.

Process for Producing $C_{2+}$ hydrocarbon mixture product using the composition of Example 3: The process practiced was same as that described under Example 1. The operating parameters for producing the $C_{2+}$ hydrocarbon mixture product was same as that practiced under Example 1. The individual catalyst components, the first catalyst component and the second catalyst component, were also tested for their efficacy in producing the $C_{2+}$ hydrocarbon mixture product by subjecting the individual catalyst components to same conditions as that of the composition of Example 3.

Results: The $C_{2+}$ hydrocarbon mixture product obtained by using the composition containing the catalyst of Example 3 $((Sr_1La_{0.9}Nd_{0.7}Yb_{0.1}O_x)_{0.1}$—$(Mn$—$Na_2WO_4/SiO_2)_{0.9})$ and that obtained from the use of the constituent first catalyst component $(Sr_1La_{0.9}Nd_{0.7}Yb_{0.1}O_x)$ and the second catalyst component $(Mn$—$Na_2WO_4/SiO_2)$ were analyzed the results obtained are tabulated below:

TABLE 8

| | Relative catalytic activity rate | | |
| --- | --- | --- | --- |
| | (Inventive) Example 3 $((Sr_1La_{0.9}Nd_{0.7}Yb_{0.1}O_x)_{0.1}$—$(Mn$—$Na_2WO_4/SiO_2)_{0.9})$ | First Catalyst Component $(Sr_1La_{0.9}Nd_{0.7}Yb_{0.1}O_x)$ | Second Catalyst Component $(Mn$—$Na_2WO_4/SiO_2)$ |
| Relative Catalytic Activity Rate | 11 | 105 | 1.0 |

TABLE 9

| | Catalyst selectivity/Product composition | | |
| --- | --- | --- | --- |
| | (Inventive) Example 3 $((Sr_1La_{0.9}Nd_{0.7}Yb_{0.1}O_x)_{0.05}$—$(Mn$—$Na_2WO_4/SiO_2)_{0.95})$ | First Catalyst Component $(Sr_1La_{0.9}Nd_{0.7}Yb_{0.1}O_x)$ | Second Catalyst Component $(Mn$—$Na_2WO_4/SiO_2)$ |
| Overall $C_{2+}$ hydrocarbon selectivity (%) | 76.5 | 74.4 | 79.7 |
| Ethyne selectivity (%) | 0.4 | 0.3 | 4.4 |
| Effective $C_{2+}$ hydrocarbon selectivity (%) | 76.1 | 74.1 | 75.3 |
| Ethylene selectivity (%) | 43.9 | 37.5 | 46.9 |
| Carbon monoxide selectivity (%) | 14.6 | 3.6 | 10.5 |
| Carbon dioxide | 9.2 | 22.0 | 9.8 |

TABLE 9-continued

| Catalyst selectivity/Product composition | | | |
|---|---|---|---|
| | (Inventive) Example 3 $((Sr_1La_{0.9}Nd_{0.7}Yb_{0.1}O_x)_{0.05}$—$(Mn$—$Na_2WO_4/SiO_2)_{0.95})$ | First Catalyst Component $(Sr_1La_{0.9}Nd_{0.7}Yb_{0.1}O_x)$ | Second Catalyst Component $(Mn$—$Na_2WO_4/SiO_2)$ |
| selectivity (%) | | | |

The results from Table 8 indicate that the catalytic activity rate of the composition comprising the catalyst of Example 3, has a higher catalytic activity rate (11) than the second catalyst component (1.0) but a lower catalytic activity rate than the first catalyst component (105.0). From Table 9, it is observed that the ethylene selectivity is improved (higher) with lower ethyne selectivity as compared to the individual catalyst components constituent the composition. Particularly, it is observed that the effective $C_{2+}$ hydrocarbon selectivity of the inventive composition is higher compared to the effective $C_{2+}$ hydrocarbon selectivity obtained from the individual components constituent the composition. It is also observed that the inventive catalyst obtained from the practice of Example 3, demonstrates improved carbon monoxide selectivity while keeping carbon dioxide selectivity low.

Example 4—Catalyst Composition Having the Formula $(Sr_1La_{0.5}Nd_{0.1}Er_{0.3}O_x)_{0.05}$—$(Ce$—$Mn$—$Na_2WO_4/SiO_2)_{0.95}$ with First Catalyst Component Present in an Amount of 5 wt. % and the Second Catalyst Component Present in an Amount of 95 wt. %

Purpose: Example 4 demonstrates the preparation and use of a composition comprising a catalyst having the formula $(Sr_1La_{0.5}Nd_{0.1}Er_{0.3}O_x)_{0.05}$—$(Ce$—$Mn$—$Na_2WO_4/SiO_2)_{0.95}$. The composition was tested for its efficacy in producing $C_{2+}$ hydrocarbon mixture product with sufficient catalytic activity rate and excellent selectivity for forming ethylene with low ethyne selectivity.

Materials: The following materials are procured and used for the synthesis of the composition.

TABLE 10

| Material Used (First Catalyst component: $Sr_1La_{0.5}Nd_{0.1}Er_{0.3}O_x$) | | | | |
|---|---|---|---|---|
| First catalyst component: $AE_aRE1_bRE2_cRE3_dO_x$ | Element used | Relative molar ratio | Precursor Material | Supplier |
| AE | Strontium (Sr) | a = 1 | Strontium Nitrate: $Sr(NO_3)_2$ | Sigma-Aldrich |
| RE1 | Lanthanum (La) | b = 0.5 | Lanthanum Nitrate $La(NO_3)_3 \cdot 6H_2O$ | Sigma-Aldrich |
| RE2 | Neodymium (Nd) | c = 0.1 | Neodymium Nitrate $Nd(NO_3)_3 \cdot 6H_2O$ | Sigma-Aldrich |
| RE3 | Erbium (Er) | d = 0.3 | Erbium Nitrate $Er(NO_3)_3 \cdot 5H_2O$ | Sigma-Aldrich |

TABLE 11

| Material Used (Second Catalyst component: $Ce_1$—$Mn$—$Na_2WO_4/SiO_2$) | | | | |
|---|---|---|---|---|
| Second catalyst component: $(M1_e$-$TM_1$-$(AM)_2WO_4/SiO_2)$ | Elements/ Material used | Weight content (%) | Precursor Material | Supplier |
| M1 | Cerium (Ce) | 5.0 (Relative molar ratio 'e' = 1) | $Ce(NO_3)_3 \cdot 6H_2O$ | Sigma-Aldrich |
| TM | Manganese (Mn) | 1.9 | Manganese Nitrate $Mn(NO_3)_2 \cdot 4H_2O$ | Sigma-Aldrich |
| $(AM)_2WO_4$ | Sodium Tungstate $(Na_2WO_4)$ | 5.0 | $Na_2WO_4 \cdot 4H_2O$ | Sigma-Aldrich |

Method for preparing the composition containing the catalyst of Example 4: The composition of Example 4, was prepared in the method similar to what was outlined under Example 1. Specifically, the method included the step of blending 0.5 g of the first catalyst component $(Sr_1La_{0.5}Nd_{0.1}Er_{0.3}O_x)$ with 9.5 g of the second catalyst component $(Ce_1-Mn-Na_2WO_4/SiO_2)$ followed by grinding and press sizing the resulting blend. The individual catalyst components, the first catalyst component and the second catalyst component were prepared as given below:

Method for Preparing the first catalyst component $(Sr_1La_{0.5}Nd_{0.1}Er_{0.3}O_x$ of Example 4: The following steps were followed for the synthesis of the first catalyst component: 8.47 g of $Sr(NO_3)_2$, 8.66 g of $La(NO_3)_3 \cdot 6H_2O$, 1.76 g of $Nd(NO_3)_3 \cdot 6H_2O$ and 5.32 g of $Er(NO_3)_3 \cdot 5H_2O$ were mixed and dissolved 40 ml water. The resulting material was dried overnight at a temperature of 125° C. and then calcined at a temperature of 900° C. for 6 hours under airflow and the first catalyst component $Sr_1La_{0.5}Nd_{0.1}Er_{0.3}O_x$ was obtained.

Method for preparing the second catalyst component $(Ce-Mn-Na_2WO_4/SiO_2)$ of Example 4: Incipient wetness method was used for the second catalyst component. Silica gel (17.6 g Davisil Grade 646) was used after drying overnight. $Mn(NO_3)_2 \cdot 4H_2O$ (1.73 g) was dissolved in deionized water (18.5 ml) and then added dropwise onto the silica gel. The resulting manganese impregnated silica material was dried overnight. $Ce(NO_3)_3 \cdot 6H_2O$ (3.10 g) was dissolved in deionized water (18.5 ml) and then added dropwise onto the manganese impregnated silica gel. $Na_2WO_4 \cdot 4H_2O$ (1.22 g) was dissolved in deionized water (18.5 ml) and the solution obtained was added onto the dried manganese impregnated silica material obtained from the above step. The resulting material was dried overnight at a temperature of 125° C. and then calcined at a temperature of 800° C. for 6 hours under airflow and the second catalyst component $Ce-Mn-Na_2WO_4/SiO_2$ was obtained.

Process for producing $C_{2+}$ hydrocarbon mixture product using the composition of Example 4: The composition obtained from the practice of Example 4 was used for producing $C_2$ hydrocarbon mixture product using the process as described under Example 1. The operating parameters for producing $C_2$ hydrocarbon mixture product was same as that described for Example 1. For the purpose of evaluating the composition comprising the catalyst of Example 4, the individual catalyst components were also tested for their efficacy in producing the $C_{2+}$ hydrocarbon mixture product. The first catalyst component $(Sr_1La_{0.5}Nd_{0.1}Er_{0.3}O_x)$ and the second catalyst component $(Ce-Mn-Na_2WO_4/SiO_2)$ were each independently subjected to the same reaction condition and process steps as that of the composition of Example 4 $(Sr_1La_{0.5}Nd_{0.1}Er_{0.3}O_x)_{0.05}-(Ce-Mn-Na_2WO_4/SiO_2)_{0.95}$.

Results: The $C_{2+}$ hydrocarbon mixture product obtained by using the composition containing the catalyst of Example 4 $(Sr_1La_{0.5}Nd_{0.1}Er_{0.3}O_x)_{0.05}-(Ce-Mn-Na_2WO_4/SiO_2)_{0.95}$ and that obtained from the use of the constituent first catalyst component $(Sr_1La_{0.5}Nd_{0.1}Er_{0.3}O_x)$ and the second catalyst component $(Ce-Mn-Na_2WO_4/SiO_2)$, were analyzed using online Gas Chromatograph having a thermal conductivity detector (TCD) and a flame ionization detector (FID). The results obtained are tabulated below:

TABLE 12

Relative catalytic activity

|  | (Inventive) Example 4 $(Sr_1La_{0.5}Nd_{0.1}Er_{0.3}O_x)_{0.05}-(Ce-Mn-Na_2WO_4/SiO_2)_{0.95}$ | First Catalyst Component $(Sr_1La_{0.5}Nd_{0.1}Er_{0.3}O_x)$ | Second Catalyst Component $(Ce-Mn-Na_2WO_4/SiO_2)$ |
|---|---|---|---|
| Relative Catalytic Activity Rate | 5.8 | 45.3 | 1.0 |

TABLE 13

Catalyst selectivity/Product composition

|  | (Inventive) Example 4 $(Sr_1La_{0.5}Nd_{0.1}Er_{0.3}O_x)_{0.05}-(Ce-Mn-Na_2WO_4/SiO_2)_{0.95}$ | First Catalyst Component $(Sr_1La_{0.5}Nd_{0.1}Er_{0.3}O_x)$ | Second Catalyst Component $(Ce-Mn-Na_2WO_4/SiO_2)$ |
|---|---|---|---|
| Overall $C_{2+}$ selectivity (%) | 79.9 | 79.1 | 79.7 |
| Ethyne selectivity (%) | 1.1 | 0.3 | 2.2 |
| Effective $C_{2+}$ hydrocarbon selectivity (%) | 78.8 | 78.8 | 77.5 |
| Ethylene selectivity (%) | 45 | 41.9 | 48.7 |
| Carbon monoxide selectivity (%) | 13.7 | 4.7 | 10.6 |
| Carbon dioxide selectivity (%) | 6.3 | 16.2 | 9.7 |

The results from Table 12, show that the catalytic activity rate of the composition comprising the catalyst of Example 4, has a higher catalytic activity rate (5.8) than the second catalyst component (1.0) but a lower catalytic activity rate than the first catalyst component (45.0). From Table 13, as is evident, the effective $C_{2+}$ hydrocarbon selectivity is higher or at same level compared to the effective $C_{2+}$ hydrocarbon selectivity obtained from the individual components. It is also observed that the inventive catalyst obtained from the practice of Example 4, demonstrates improved carbon monoxide selectivity while keeping carbon dioxide selectivity low. This is particularly advantageous as carbon monoxide can be reconverted back to more useful chemical products while mitigating the extent of carbon dioxide emission.

Example 5—(Variant of the Example 4) Catalyst Composition Having the Formula $(Sr_1La_{0.5}Nd_{0.4}Er_{0.3}O_x)_{0.05}$—$(Ce-Mn-Na_2WO_4/SiO_2)_{0.95}$ with First Catalyst Component Present in an Amount of 5 wt. % and the Second in an Amount of 95 wt. %

Purpose: Example 5 demonstrates the preparation and use of a composition comprising a catalyst having the formula $(Sr_1La_{0.5}Nd_{0.1}Er_{0.3}O_x)_{0.05}$—$(Ce-Mn-Na_2WO_4/SiO_2)_{0.95}$. The composition obtained from the practice of Example 5 differs from that of Example 4, by way of preparing the constituent second catalyst component involving the use of silica sol with 34% of silica content and a starting material involving nanostructured manganese oxide. As silica sol was used for preparation of the second catalyst component, slurry preparation method was used for this example.

Materials: The material used was same as reported under Example 4 except that a silica sol with 34% of silica content and a nanostructured manganese oxide was used for preparing the second catalyst component.

Method for preparing the composition containing the catalyst of Example 5: The composition containing the blended product of the first catalyst component and the second catalyst component was prepared in the same method as described under Example 1 or 4. The individual catalyst components, were prepared as given: Method for Preparing the first catalyst component $(Sr_1La_{0.5}Nd_{0.1}Er_{0.3}O_x)$ of Example 5: The first catalyst component of Example 5 was prepared in the same manner as described for the first catalyst component of Example 4. Method for preparing the second catalyst component $(Ce-Mn-Na_2WO_4/SiO_2)$ of Example 5: Slurry preparation method was used for this second catalyst component. Nanostructured Manganese Oxide (1.89 g wet cake containing 10% $MnO_2$) was dispersed in 10 ml deionized water. The slurry so obtained was mixed with 13.7 g of a silica sol (with 34% silica). 1.54 g of $Ce(NO_3)_3 \cdot 6H_2O$ was dissolved in 50 ml water and was subsequently added to the slurry and agitated at 90° C. for 2 hours. The resulting material was dried overnight at a temperature of 125° C. overnight. Then, 0.50 g of $Na_2WO_4$ with sheet structure was mixed with the dried material obtained above, followed by calcination at 800° C. for 6 hours. The second catalyst component, $Ce-Mn-Na_2WO_4/SiO_2$ was obtained. The weight content of Cerium (Ce) was found to be 8.7 wt %, manganese (Mn) was found to be 2.1 wt. % and the weight content of sodium tungstate ($Na_2WO_4$) was found to be 7.8 wt. %.

Process for producing $C_{2+}$ hydrocarbon mixture product using the composition of Example 5: The composition obtained from the practice of Example 5 was used for producing $C_{2+}$ hydrocarbon mixture product using the process and conditions as described under Example 1. The operating parameters for producing the $C_{2+}$ hydrocarbon mixture product were same as that of Example 1. For the purpose of evaluating the composition comprising the catalyst of Example 5, the individual catalyst components were also tested for their efficacy in producing the $C_{2+}$ hydrocarbon mixture product. The first catalyst component $(Sr_1La_{0.5}Nd_{0.1}Er_{0.3}O_x)$ and the second catalyst component $(Ce-Mn-Na_2WO_4/SiO_2)$ were each independently subjected to the same reaction condition and process steps as that of the composition of Example 5 $(Sr_1La_{0.5}Nd_{0.1}Er_{0.3}O_x)_{0.05}$—$(Ce-Mn-Na_2WO_4/SiO_2)_{0.95}$.

Results: The $C_2$ hydrocarbon mixture product obtained using the composition containing catalyst of Example 5 $(Sr_1La_{0.5}Nd_{0.1}Er_{0.3}O_x)_{0.05}$—$(Ce-Mn-Na_2WO_4/SiO_2)_{0.95}$ and that obtained from the use of the constituent first catalyst component $(Sr_1La_{0.5}Nd_{0.1}Er_{0.3}O_x)$ and the second catalyst component $(Ce-Mn-Na_2WO_4/SiO_2)$ were analyzed and reported below:

TABLE 14

| | Relative catalytic activity rate | | |
|---|---|---|---|
| | (Inventive) Example 5 $(Sr_1La_{0.5}Nd_{0.1}Er_{0.3}O_x)_{0.05}$—$(Ce-Mn-Na_2WO_4/SiO_2)_{0.95}$ | First Catalyst Component $(Sr_1La_{0.5}Nd_{0.1}Er_{0.3}O_x)$ | Second Catalyst Component $(Ce-Mn-Na_2WO_4/SiO_2)$ |
| Relative Catalytic Activity Rate | 5.8 | 87.8 | 1.0 |

TABLE 15

Catalyst selectivity/Product composition

| | (Inventive) Example 5 $(Sr_1La_{0.5}Nd_{0.1}Er_{0.3}O_x)_{0.05}$—(Ce—Mn—Na$_2$WO$_4$/ SiO$_2$)$_{0.95}$ | First Catalyst Component $(Sr_1La_{0.5}Nd_{0.1}Er_{0.3}O_x)$ | Second Catalyst Component (Ce—Mn—Na$_2$WO$_4$/SiO$_2$) |
|---|---|---|---|
| Overall $C_{2+}$ hydrocarbon selectivity (%) | 82.4 | 79.1 | 82.6 |
| Ethyne selectivity (%) | 0.4 | 0.3 | 4.1 |
| Effective $C_{2+}$ hydrocarbon selectivity (%) | 82.0 | 78.8 | 78.5 |
| Ethylene selectivity (%) | 45.1 | 41.9 | 47.7 |
| Carbon monoxide selectivity (%) | 13.4 | 4.7 | 8.0 |
| Carbon dioxide selectivity (%) | 4.2 | 16.2 | 9.4 |

The results from Table 14, show that the catalytic activity rate of the composition comprising the catalyst of Example 5, has a higher catalytic activity rate (5.8) than the second catalyst component (1.0) but a lower catalytic activity rate than the first catalyst component (45.0). From Table 15, as is evident, the effective $C_{2+}$ hydrocarbon selectivity is higher compared to the effective $C_{2+}$ hydrocarbon selectivity obtained by the use of the individual components. In addition, the inventive composition demonstrates relatively high carbon monoxide selectivity while the selectivity for carbon dioxide is low, compared to the individual components constituent the inventive composition. This is particularly advantageous for improving the productivity of the catalyst as carbon monoxide can be converted back to more useful chemical products while carbon dioxide cannot be so converted and becomes a waste by product.

Example 6 (Comparative) Catalyst Composition Having the Formula $Sr_1La_{0.9}Nd_{0.7}Yb_{0.1}O_x)_{0.3}$—(Mn—Na$_2$WO$_4$/SiO$_2$)$_{0.7}$ with the First Catalyst Component Present in an Amount of 30 wt. % and the Second Catalyst Component in an Amount of 70 wt. %

Purpose: Example 6 is a comparative example and is used for comparing and contrasting the results obtained from the inventive examples Example 1-5. Example 6 demonstrates the need to blend the first catalyst component and the second catalyst component in a proportion that results in a composition containing a catalyst with sufficient activity rate and improved selectivity towards ethylene while maintaining low ethyne selectivity.

Materials: The material used is same as that described under Example 1. The operating parameters were kept same as that of Example 1.

Method for preparing a composition containing the catalyst of Example 6: The process practiced was same as that described under Example 1 except that 3 g of $Sr_1La_{0.9}Nd_{0.7}Yb_{0.1}O_x$ was blended with 7 g of Mn—Na$_2$WO$_4$/SiO$_2$ to form the composition. The individual catalyst components, first catalyst component and the second catalyst component, were prepared using the same method as those described under Example 1.

Process for producing $C_2$ hydrocarbon mixture product using the composition of Example 6: The process practiced was same as that described under Example 1. The individual catalyst components were also tested for their efficacy in producing the $C_{2+}$ hydrocarbon mixture product as described under any of the examples, Example 1-5. The operating parameters for producing the $C_{2+}$ hydrocarbon mixture product were same as that practiced under Example 1:

Results: The $C_{2+}$ hydrocarbon mixture product obtained using the composition containing catalyst of Example 6 $((Sr_1La_{0.9}Nd_{0.7}Yb_{0.1}O_x)_{0.3}$—(Mn—Na$_2$WO$_4$/SiO$_2$)$_{0.7}$) and that obtained from the use of the constituent first catalyst component $(Sr_1La_{0.9}Nd_{0.7}Yb_{0.1}O_x)$ and the second catalyst component (Mn—Na$_2$WO$_4$/SiO$_2$) were analyzed, the results obtained are tabulated below:

TABLE 16

Relative catalytic activity rate

| | (Inventive) Example 6 $((Sr_1La_{0.9}Nd_{0.7}Yb_{0.1}O_x)_{0.3}$—(Mn—Na$_2$WO$_4$/ SiO$_2$)$_{0.7}$) | First Catalyst Component $(Sr_1La_{0.9}Nd_{0.7}Yb_{0.1}O_x)$ | Second Catalyst Component (Mn—Na$_2$WO$_4$/SiO$_2$) |
|---|---|---|---|
| Relative Catalytic Activity Rate | 35 | 105 | 1.0 |

TABLE 17

| | (Inventive) Example 6 $((Sr_1La_{0.9}Nd_{0.7}Yb_{0.1}O_x)_{0.3}$—$(Mn$—$Na_2WO_4/SiO_2)_{0.7})$ | First Catalyst Component $(Sr_1La_{0.9}Nd_{0.7}Yb_{0.1}O_x)$ | Second Catalyst Component $(Mn$—$Na_2WO_4/SiO_2)$ |
|---|---|---|---|
| Overall $C_{2+}$ selectivity (%) | 68.2 | 74.4 | 79.7 |
| Effective $C_{2+}$ hydrocarbon selectivity (%) | 68.1 | 74.1 | 75.3 |
| Ethyne selectivity (%) | 0.1 | 0.3 | 4.4 |
| Ethylene selectivity (%) | 27.4 | 37.5 | 46.9 |
| Carbon monoxide selectivity (%) | 11.4 | 3.6 | 10.5 |
| Carbon dioxide selectivity (%) | 20.4 | 22.0 | 9.8 |

It is evident from Table 17, that the composition of Example 6 does not offer any specific advantage over the constituent components as the ethylene selectivity and the effective $C_{2+}$ hydrocarbon selectivity for the composition of Example 6 is substantially lower than the first catalyst component and the second catalyst component. Particularly, the selectivity towards ethylene for the composition of Example 6, is about 27% lower than that of the first catalyst component and 42% lower than that of the second catalyst component while the effective $C_{2+}$ hydrocarbon selectivity for the composition of Example 6 is about 9% lower than that of the first catalyst component and about 11% lower than that of the second catalyst component. Further as will be evident from Table 17 below, the composition of Example 6 has a much lower performance in terms of ethylene and effective $C_{2+}$ hydrocarbon selectivity compared to the compositions from Example 1-5. Further, the catalyst composition demonstrates high carbon dioxide selectivity which results in the production of large amounts of carbon dioxide which is a waste by-product. It may be concluded, that the proportion of the first catalyst component and the second catalyst component should be at a specific proportion to form the inventive composition having the desired attribute of producing $C_{2+}$ hydrocarbons with high ethylene selectivity and low ethyne selectivity.

Example 7—Testing the Stability for the Catalyst Composition Having the Formula $(Sr_1La_{0.5}Nd_{0.1}Er_{0.3}O_x)_{0.05}$—$(Ce$—$Mn$—$Na_2WO_4/SiO_2)_{0.95}$ with First Catalyst Component Present in an Amount of 5 wt % and the Second Catalyst Component Present in an Amount of 95 wt. %

Purpose: Example 7 demonstrates an improved catalytic stability of a composition comprising a catalyst, prepared as an embodiment of the invention.

Material: The material used was the composition obtained from the practice of Example 4 $(Sr_1La_{0.5}Nd_{0.1}Er_{0.3}O_x)_{0.05}$—$(Ce$—$Mn$—$Na_2WO_4/SiO_2)_{0.95}$ and a composition containing a catalyst represented by the formula $Mn$—$Na_2WO_4/SiO_2$, used as a control.

Procedure: The composition comprising the catalyst represented by $(Sr_1La_{0.5}Nd_{0.1}Er_{0.3}O_x)_{0.05}$—$(Ce$—$Mn$—$Na_2WO_4/SiO_2)_{0.95}$ was introduced in a quartz reactor and was subjected to reactor conditions where a feed mixture comprising methane and oxygen, at a ratio of 7.4:1 was introduced at a gas hourly space velocity (GHSV) of 37,500 $hr^{-1}$. The temperature was maintained at ~810° C. and an ambient pressure as described in Example 1. The composition containing a catalyst represented by the formula $Mn$—$Na_2WO/SiO_2$ was independently introduced in another quartz reactor and was exposed to a feed mixture of methane and oxygen at a ratio of 7.4:1 at a gas hourly space velocity (GHSV) of 12,000 $hr^{-1}$. The catalyst compositions were monitored for 14 hours and the results related to the oxygen conversion by both the compositions were analyzed in detail.

Figure 3:
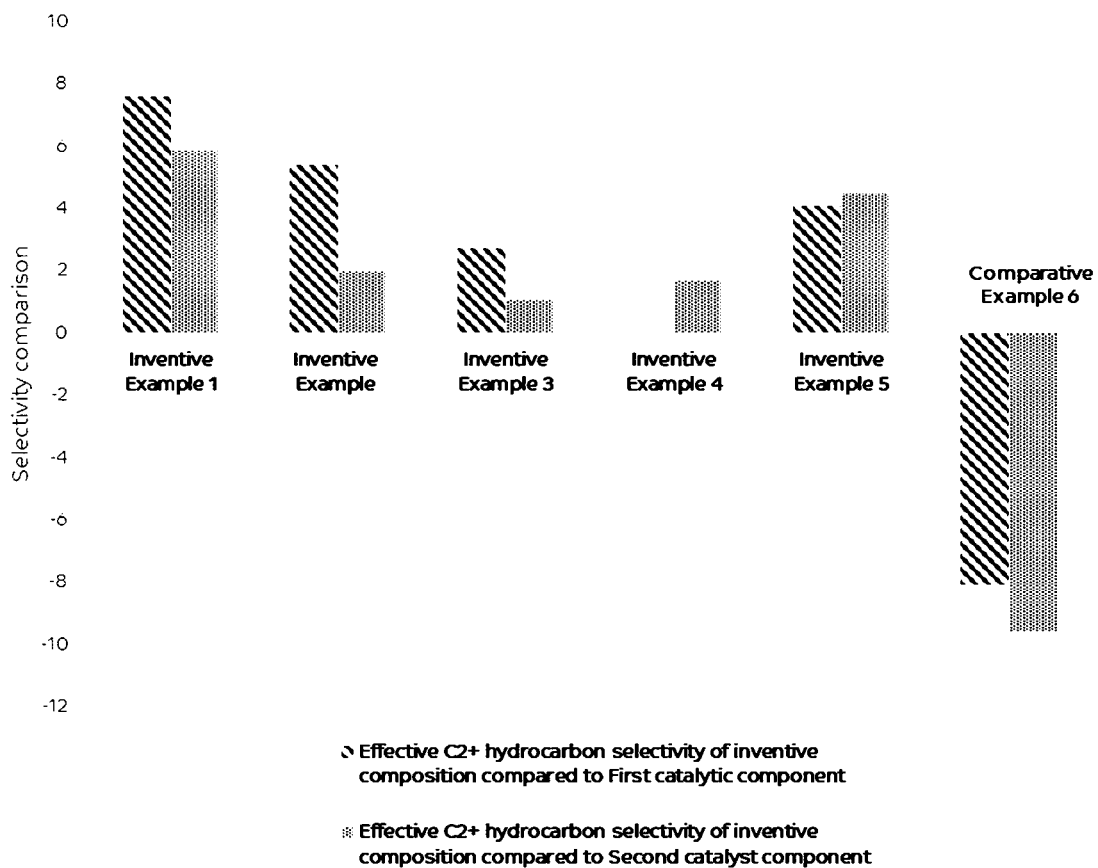
FIG. 3 is a graphical representation of the effective $C_{2+}$ hydrocarbon obtained from the compositions formed from the practice of Example 1-6 and compared with its constituent components.

Result: FIG. 3 graphically represents the results obtained from the practice of Example 7. The results are compared and tabulated as shown below:

TABLE 18

| | Deactivation rate (1/hr) | |
|---|---|---|
| | $(Sr_1La_{0.5}Nd_{0.1}Er_{0.3}O_x)_{0.05}$—$(Ce$—$Mn$—$Na_2WO_4/SiO_2)_{0.95}$ | $Mn$—$Na_2WO_4/SiO_2$ (Control) |
| Deactivation rate (1/hr) | 0.017 | 0.026 |

Figure 4:
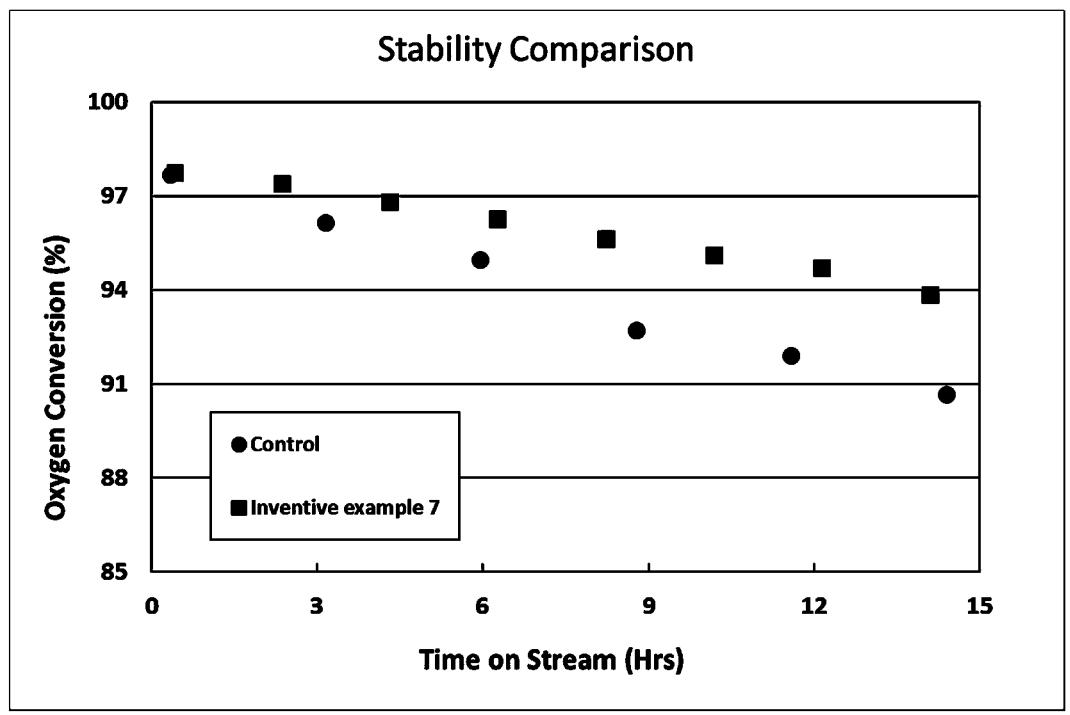
FIG. 4 is a graphical representation of the comparison of the oxygen conversion of an inventive composition prepared from Example 4 with that of a control, under conditions of high reactor severity.

From Table 18 and as illustrated in FIG. 4, it is surprisingly found that the inventive composition was able to retain its activity even at severe reactor conditions indicating high catalyst stability. The inventive composition $(Sr_1La_{0.5}Nd_{0.1}Er_{0.3}O_x)_{0.05}$—$(Ce-Mn-Na_2WO_4/SiO_2)_{0.95}$ was exposed to feed mixture at three times higher GHSV as compared to the composition $Mn-Na_2WO/SiO_2$. The high oxygen conversion for the inventive composition $(Sr_1La_{0.5}Nd_{0.1}Er_{0.3}O_x)_{0.05}$—$(Ce-Mn-Na_2WO_4/SiO_2)_{0.95}$ was retained even when exposed over a prolonged period of time and at a high reactor severity. The inventive composition demonstrates a deactivation rate of nearly 35% slower than the composition $Mn-Na_2WO_4/SiO_2$. Based on the results, it may be concluded that the inventive composition is able to demonstrate a much higher stability than the composition $Mn-Na_2WO_4/SiO_2$.

Summary of the results: The results obtained from the practice of the inventive examples, (Example 1-5) are compared with the result obtained from the practice of the comparative example (Example 6) and summarized under Table 19. The composition obtained from the practice of a particular example is denoted as "Composition" while the constituent components, first catalyst component and the second catalyst component are denoted as "CI" and "CII" respectively.

TABLE 19

Summary of results from Examples 1-6

|  | Components | Catalytic Activity Rate | Ethylene selectivity (%) | Effective $C_{2+}$ hydrocarbon selectivity | Ethyne selectivity (%) | Overall $C_{2+}$ hydrocarbon selectivity (%) |
| --- | --- | --- | --- | --- | --- | --- |
| Inventive Example 1 | Composition | 5.9 | 46 | 79.7 | 1.1 | 80.8 |
|  | CI | 105 | 37.5 | 74.1 | 0.3 | 74.4 |
|  | CII | 1 | 46.9 | 75.3 | 4.4 | 79.7 |
| Inventive Example 2 | Composition | 58.5 | 42.2 | 78.1 | 0.4 | 78.5 |
|  | CI | 147.8 | 37.5 | 74.1 | 0.3 | 74.4 |
|  | CII | 1 | 47.3 | 76.6 | 3.6 | 80.2 |
| Inventive Example 3 | Composition | 11 | 43.9 | 76.1 | 0.4 | 76.5 |
|  | CI | 105 | 37.5 | 74.1 | 0.3 | 74.4 |
|  | CII | 1 | 46.9 | 75.3 | 4.4 | 79.7 |
| Inventive Example 4 | Composition | 5.8 | 45 | 78.8 | 1.1 | 79.9 |
|  | CI | 45.3 | 41.9 | 78.8 | 0.3 | 79.1 |
|  | CII | 1.0 | 48.7 | 77.5 | 2.2 | 79.7 |
| Inventive Example 5 | Composition | 5.8 | 45.1 | 82 | 0.4 | 82.4 |
|  | CI | 87.8 | 41.9 | 78.8 | 0.3 | 79.1 |
|  | CII | 1 | 47.7 | 78.5 | 4.1 | 82.6 |
| Comparative Example 6 | Composition | 35.0 | 27.4 | 68.1 | 0.1 | 68.2 |
|  | CI | 105 | 37.5 | 74.1 | 0.3 | 74.4 |
|  | CII | 1 | 46.9 | 75.3 | 4.4 | 79.7 |

Figure 2:
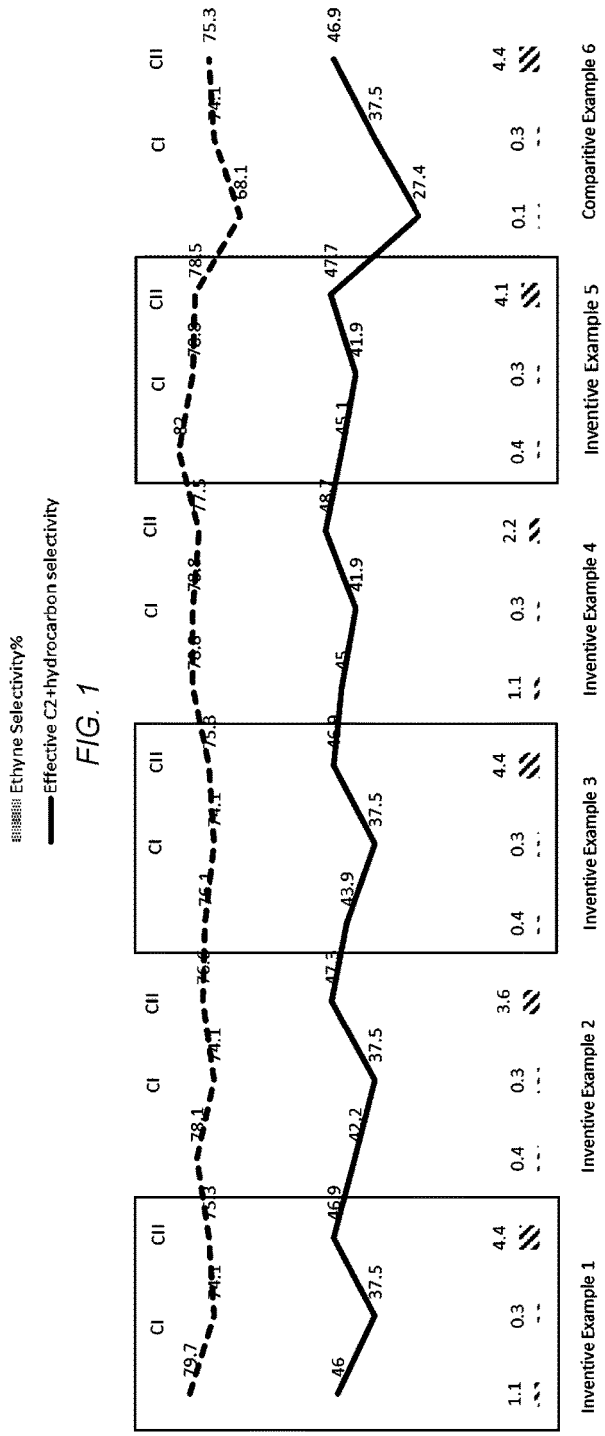
FIG. 2 is a graphical representation of the comparison of ethylene and ethyne selectivity of the compositions obtained from the practice of Examples 1-6 with that of the individual components.

The results summarized under Table 19 and graphically illustrated under FIG. 1 indicate that the inventive compositions obtained from the practice of Example 1-5, provide previously unseen benefits of high ethylene selectivity while maintaining low ethyne selectivity and a sufficient catalytic activity rate suitable for the production of $C_{2+}$ hydrocarbon mixture product. The ethylene selectivity for the inventive compositions from Example 1-5, are at least 35% higher than that of the composition obtained from the practice of the comparative example (Example 6). Advantageously, as is evident from Table 19, the inventive compositions have an effective $C_{2+}$ hydrocarbon selectivity nearly 11% higher than that obtained from the practice of the comparative Example 6 thereby indicating that the inventive compositions are better suited to produce high value hydrocarbon products with minimal purification. In addition, it is observed that the inventive compositions from Example 1-5, have improved carbon monoxide selectivity while maintaining relatively low carbon dioxide selectivity. This is particularly useful as carbon monoxide can always be reconverted back to more useful $C_{2+}$ hydrocarbons while carbon dioxide cannot be. Further the lower amount of carbon dioxide generated makes the processes using the inventive composition produced from this invention, environmentally more sustainable. The attribute of having high ethylene selectivity while maintaining low ethyne selectivity, is particularly beneficial for using the inventive catalyst composition for the industrial production of ethylene and its derivatives which can be subsequently used for producing polyethylene. Further, from the results obtained by the practice of Example 7, unexpectedly exhibited previously unseen attributes of having high catalyst stability even at high reactor severity especially when using the composition for conducting catalysis at high temperature such as the catalysis of oxidative coupling of methane. As is evident from FIG. 2, it may be further concluded that the beneficial attributes of the inventive compositions from Example 1-5, is brought about by a synergistic combination of the constituent catalyst components (CI &CII) when blended in a specific proportion. This conclusion is further affirmed by analyzing the performances of the individual components for the composition obtained from the practice of Examples 1, 2, 3 and 6. For all the four compositions, the constituents are the same, except for the proportion in which the first catalyst component and the second catalyst component are blended together.

The invention claimed is:

1. A composition, comprising a blended product of: (a) a first catalyst component comprising an alkaline earth metal and at least one rare earth element, the first catalyst component having an initial first catalytic activity rate and is present in an amount more than 0 wt. % to about 25 wt. % of the total weight of the composition; and (b) a second catalyst component comprising a transition metal element having redox property and an alkali metal tungstate compound, the second catalyst component having an initial second catalytic activity rate and is present in an amount, greater than about 75 wt. % of the total weight of the composition; wherein, the composition has a catalytic activity rate that is more than the initial second catalytic activity rate and less than the initial first catalytic activity rate.

2. The composition of claim 1, wherein the composition has a catalytic activity rate ranging from about 5 times to about 60 times of the initial second catalytic activity rate and the initial first catalytic activity rate ranging from about 5 times to about 150 times of the initial second catalytic activity rate.

3. The composition of claim 1, wherein the first catalyst component is present in an amount of from about 4 wt. % to about 15 wt. %, of the total weight of the composition.

4. The composition of claim 1, wherein the first catalyst component is represented by a general formula (I): $AE_aRE1_bRE2_cAT_dO_x$ wherein (a) 'AE' represents an alkaline earth metal; (b) 'RE1' represents a first rare earth element; (c) 'RE2' represents a second rare earth element; and (d) 'AT' represents a first redox agent or a third rare earth element (RE3); wherein, 'a', 'b', 'c' and 'd' represents relative molar ratio; wherein 'a' is 1; 'b' ranges from about 0.1 to about 10; 'c' ranges from about 0.01 to about 10; 'd' ranges from 0 to about 10; 'x' balances the oxidation state; wherein, the first rare earth element, the second rare earth element and the third rare earth element, are different.

5. The composition of claim 4, wherein the alkaline earth metal is selected from the group consisting of magnesium, calcium, strontium, barium, and combinations thereof.

6. The composition of claim 4, wherein the first rare earth element, the second rare earth element, the third rare earth element and the fourth rare earth element are each independently selected from the group consisting of lanthanum, scandium, cerium, praseodymium, neodymium, promethium, samarium, europium, gadolinium, yttrium, terbium, dysprosium, holmium, erbium, thulium, ytterbium, lutetium, and combinations thereof.

7. The composition of claim 4, wherein the first redox agent, the second redox agent and the third redox agent are each independently selected from the group consisting of manganese, tungsten, bismuth, antimony, tin, cerium, praseodymium, vanadium, chromium, iron, cobalt and combinations thereof.

8. The composition of claim 1, wherein the second catalyst component is of formula (II): $(M1_e\text{-TM-}(AM)_2WO_4/SiO_2)$ wherein: (a) 'M1' represents a second redox agent or a fourth rare earth element (RE4) and is present in an amount ranging from 0 wt. % to about 10 wt. %; (b)$(AM)_2WO_4$ represents an alkali metal tungstate selected from the group consisting of lithium tungstate, sodium tungstate, potassium tungstate, rubidium tungstate, caesium tungstate and combinations thereof, and is present in an amount ranging from more than 0 wt. % to about 10 wt. %; (c) 'TM' represents a third redox agent and is present in an amount ranging from more than 0 wt. % to about 10 wt. %; (d) 'e' ranges from 0 to about 10; wherein, 'M1' and 'TM' are different elements.

9. The composition of claim 1, wherein the composition has an ethyne selectivity ranging from more than 0 to 2% of product formed and an ethylene selectivity of at least 42% of product formed, when the composition is used in a process that makes $C_{2+}$ hydrocarbon mixture product from methane.

10. The composition of claim 9, wherein ethylene selectivity ranges from 42% to 65% of product formed when the composition is used in a process that makes $C_{2+}$ hydrocarbon mixture product from methane.

11. The composition of claim 1, wherein the composition has an effective $C_{2+}$ hydrocarbon selectivity ranging from 1% to 10% greater than effective $C_{2+}$ hydrocarbon selectivity of the second catalyst component.

12. The composition of claim 1, wherein the composition has a carbon dioxide selectivity less than 15% of product formed when the composition is used in a process that makes $C_{2+}$ hydrocarbon mixture product from methane.

13. The composition of claim 1, wherein the composition has a deactivation rate at least 30% slower than the second catalyst component.

14. A method for preparing the composition of claim 1, comprising (a)
blending more than 0 to about 25 wt. % of the first catalyst component with greater than about 75 wt. % of the second catalyst component, and (b) forming the composition.

15. A composition comprising a $C_{2+}$ hydrocarbon mixture product, wherein the composition is formed using the composition of claim 1; optionally wherein the $C_{2+}$ hydrocarbon mixture product comprises ethylene, ethane, ethyne, propene, propane, $C_4$-$C_5$ hydrocarbons, carbon dioxide, carbon monoxide and combinations thereof.

16. A process for producing a $C_{2+}$ hydrocarbon mixture product comprising the steps of (a) introducing a feed mixture comprising methane and oxygen in a reactor containing the composition of claim 1; (b) subjecting the feed mixture to a methane coupling reaction under conditions to produce the $C_{2+}$ hydrocarbon mixture product; and (c) recovering the $C_2$ hydrocarbon mixture product after removing unconverted methane and steam from the $C_{2+}$ hydrocarbon mixture product; optionally wherein methane to oxygen ratio ranges from about 2:1 to about 15:1; optionally wherein the $C_{2+}$ hydrocarbon mixture product is produced at a reactor temperature ranging from about 400° C. to about 900° C.

17. A composition, comprising a blended product having: (i) a first catalyst component represented by a general formula (I): $AE_aRE1_bRE2_cAT_dO_x$ wherein (a) 'AE' is an alkaline earth metal; (b) 'RE1' is a first rare earth element; (c) 'RE2' represents a second rare earth element; (d) 'AT' is a first redox agent or a third rare earth element (RE3); wherein, 'a' is 1; 'b' ranges from about 0.1 to about 10; 'c' ranges from about 0.01 to about 10; 'd' ranges from 0 to about 10; 'x' balances the oxidation state; wherein the first rare earth element (RE1), the second rare earth element (RE2) and the third rare earth element (RE3), are different; wherein, the first catalyst component has an initial first catalytic activity rate and is present in an amount more than 0 to about 25 wt. % of the composition; and (ii) a second catalyst component represented by the general formula (II): $(M1_e\text{-TM-}(AM)_2WO_4/SiO_2)$ wherein (a) 'M1' is a second redox agent or a fourth rare earth element (RE4) and is present in an amount ranging from 0 wt. % to about 10 wt. %; (b) $(AM)_2WO_4$ is an alkali metal tungstate selected from the group consisting of lithium tungstate, sodium tungstate, potassium tungstate, rubidium tungstate, caesium tungstate and combinations thereof, and is present in an amount ranging from more than 0 to about 10 wt. %; (c) 'TM' is a third redox agent and is present in an amount ranging from more than 0 to about 10 wt. %; and (d) 'e' ranges from 0 to about 10; wherein 'M1' and 'TM' are different elements; wherein, the second catalyst component has an initial second catalytic activity rate and is present in an amount greater than about 75 wt. % of the composition; wherein, the composition has a catalytic activity rate that is more than the initial second catalytic activity rate and less than the initial first catalytic activity rate; wherein, the composition has an ethyne selectivity ranging from more than 0 to 2% of product formed and an ethylene selectivity of at least 42% of product formed, when the composition is used in a process that makes $C_{2+}$ hydrocarbon mixture product from methane.

* * * * *